United States Patent [19]
Adair et al.

[11] Patent Number: 5,432,165
[45] Date of Patent: Jul. 11, 1995

[54] METHODS FOR THE TREATMENT OF INFECTION CAUSED BY HEPATITIS B VIRUS (HBV)

[75] Inventors: Dennis W. Adair, Suisun, Calif.; Kenneth A. Smiles, Loveland, Ohio; Dannie H. King, Solano Beach, Calif.

[73] Assignee: Oclassen Pharmaceuticals, Inc., San Raphael, Calif.

[21] Appl. No.: 959,004

[22] Filed: Oct. 9, 1992

Related U.S. Application Data

[63] Continuation-in-part of Ser. No. 952,927, Sep. 25, 1992, abandoned, which is a continuation-in-part of Ser. No. 863,890, Apr. 6, 1992, abandoned.

[51] Int. Cl.6 ............................................. A61K 31/505
[52] U.S. Cl. ............................................. 514/50; 514/49
[58] Field of Search ...................... 536/28.54, 28.55; 514/49, 50

[56] References Cited

U.S. PATENT DOCUMENTS

| | | | |
|---|---|---|---|
| 4,211,773 | 7/1980 | Lopez et al. | 514/49 |
| 4,594,339 | 6/1986 | Lopez et al. | 514/42 |
| 4,666,892 | 5/1987 | Fox et al. | 514/49 |

FOREIGN PATENT DOCUMENTS

0147774  2/1976  Germany .................. 514/50

OTHER PUBLICATIONS

Fried, M. W. et al.; *Hematology*, vol. 16, No. 4 Pt. 2 (1992), p. 127 A.
Hantz, O. et al.; *Antiviral Research*, vol. 4, No. 4 (1984), pp. 187–199.

*Primary Examiner*—Douglas W. Robinson
*Assistant Examiner*—James O. Wilson
*Attorney, Agent, or Firm*—Pennie & Edmonds

[57] ABSTRACT

The present invention relates to pharmaceutical compositions useful for the treatment of subjects suffering from an infection or disease caused by the hepatitis B virus (HBV). In particular, it has been discovered that the administration of low dosage amounts of 1-(2'-deoxy-2'-fluoro-$\beta$-D-arabinofuranosyl)-5-iodouracil (FIAU) to humans chronically infected with HBV is effective to reduce drastically circulating markers associated with HBV. The present invention is also directed to methods of the preparation of pharmaceutical antiviral compositions.

13 Claims, 16 Drawing Sheets

METHODS FOR THE TREATMENT OF INFECTION CAUSED BY HEPATITIS B VIRUS (HBV)

CROSS REFERENCE TO RELATED APPLICATIONS

The present application is a continuation-in-part of prior, U.S. application Ser. No. 07/952,927, filed Sep. 25, 1992, now abandoned, which in turn, is a continuation in part of prior, U.S. application Ser. No. 07/863,890, filed Apr. 6, 1992, now abandoned, the complete disclosures of which are incorporated by reference herein.

FIELD OF THE INVENTION

The present invention relates to pharmaceutical compositions useful for the treatment of human subjects suffering from an infection or disease caused by the hepatitis B virus (HBV). In particular, human subjects who suffer from a chronic HBV infection, including those suffering concurrently from other medical conditions, such as an infection, disease or other pathological condition caused by the human immunodeficiency virus (HIV), can benefit from a therapeutic regimen which includes the administration of the compositions of the present invention.

BACKGROUND OF THE INVENTION

The nucleoside compound 1-(2'-deoxy-2'-fluoro-$\beta$-D-arabinofuranosyl)-5-iodouracil (FIAU) has been described, for example, in U.S. Pat. No. 4,211,773, as an antiviral and an antitumor agent. The disclosure of this patent reference includes methods for the preparation of the compound FIAU and also claims pharmaceutical compositions comprising a general class of pyrimidine analogs, including FIAU, 1-(2'-deoxy-2'-fluoro-$\beta$-D-arabinofuranosyl)-5-iodocytosine (FIAC) or pharmaceutically acceptable acid addition salts thereof. In vitro data showing the inhibition of Herpes Simplex Virus (HSV) replication are presented for a variety of nucleoside analogs. In the case of FIAC, in vivo data of mice inoculated with HSV-1 are also presented, showing improved survival rates for those test animals that received FIAC compared with control animals.

Other studies involving the in vitro activity of FIAC and its primary deaminated uracil metabolite, FIAU, against several herpes group viruses, particularly herpes simplex (HSV) types 1 and 2, varicella zoster (VZV), and cytomegalovirus (CMV) have been performed. Although not elucidated in definitive detail, FIAC/FIAU (it should be apparent to the reader that, alternatively, FIAC can be considered the prodrug of FIAU) apparently exert their effect by serving as substrates for viral DNA polymerase. (Cheng, Y.-C. et al. *Antimicrobial Agents and Chemotherapy* 1981, 20:420–423.) The in vitro $ED_{90}$ value for FIAC/FIAU against these viruses ranges from approximately 0.05 $\mu$M for HSV-1 to about 0.5 $\mu$M for CMV. Typical cellular toxicity concentrations ($ID_{50}$) are approximately in the 10 $\mu$M range. (Lopez, C. et al. *Antimicrobial Agents and Chemotherapy* 1980, 17(5):803–806; Schinazi, R. F. et al. *Antimicrobial Agents and Chemotherapy* 1986, 29:77–84; Colacino, J. M. et al. *Antimicrobial Agents and Chemotherapy* 1983, 24:505–508; Hantz, O. et al. *Antiviral Research* 1984, 4:187–189).

Previous Clinical Studies

In previous studies to determine the effectiveness of FIAC against herpes group viruses, involving more than 100 patients, including immune-compromised patients, FIAC was found to be nearly completely absorbed following oral administration and was very rapidly converted to FIAU. The half-life of FIAU was sufficiently long to allow for effective antiviral concentrations $>0.2$ $\mu$M to be present in the plasma for 8 to 12 hours after an oral dose of FIAC of $\leq 2.5$ mg/kg that was not acutely toxic. (Feinberg, A. et al. *Antimicrobial Agents and Chemotherapy* 1985, 27:733–738.) Due to the severe nature of disease in these very debilitated patients, high doses ($\sim$10–20 mg/kg-day) of FIAC were used and it proved very difficult and often impossible to distinguish drug toxicity from the natural course of these extremely ill patients.

These studies showed that the active anti-herpetic compound in the plasma is FIAU. FIAC was almost never detected two hours after dosing, verifying its rapid deamination to FIAU. FIAU peak levels averaged approximately 0.5 $\mu$g/ml, were consistent between patients, and stable from Day 3 of dosing onward. The trough values had the same characteristics, except that they averaged approximately 0.05 $\mu$g/ml. Values of FAU were low, dose dependent ($\sim$0.05 $\mu$g/ml at 0.6 mg/kg-day vs $\sim$0.10 $\mu$g/ml at 1.0 mg/kg-day) and did not increase with continued dosing. These results confirmed that FIAU is the predominant anti-herpetic compound present in the plasma, and that neither FIAC, FIAU, or their metabolites accumulated in the plasma during month long TID dosing.

FIAU is the primary metabolite of FIAC and the administration of the metabolite simplifies the metabolism involved by eliminating the direct conversion of FIAC to FAC, a potentially more toxic metabolite. (Philips, F. S. et al. *Cancer Research* 1983, 43:3619–3627.)

In Vitro and Animal Model Studies of Anti-HBV Activity

Hantz et al. demonstrated in two in vitro systems that FIAC inhibited the activity of the DNA polymerase enzyme of both human hepatitis B virus and woodchuck hepatitis virus by 50 percent at a concentration of 0.05–0.1 $\mu$M. (Hantz, O. et al. *Antiviral Research* 1984, 4:187–189.)

Fourel et al. dosed woodchucks infected with woodchuck hepatitis virus, a virus closely related to hepatitis B, for 7 days with FIAC at 20 mg/kg-day. (Fourel, I. et al. *Antimicrobial Agents and Chemotherapy* 1990, 34:473–475.) Rapid, complete and persistent suppression of both viral polymerase and DNA were observed. A similar dose of ara-AMP given for 14 days also suppressed viral DNA but was followed by a rapid rebound to levels above baseline, a pattern similar to that seen in earlier clinical trials of this agent. (Hoofnagle, J. H. and Di Bisceglie, A. M. "Antiviral Therapy of Viral Hepatitis" in *Antiviral Agents and Viral Diseases of Man.* Galasso, G. J. et al. (Eds.), 3rd Edition, Raven Press, New York (1989), pp. 415–460.)

The use of 1-(2'-deoxy-2'-substituted-b-D-arabinofuranosyl)-5-substituted pyrimidines in methods for the treatment of hepatitis B virus infection and woodchuck hepatitis virus infection is also disclosed in U.S. Pat. No. 4,666,892 ('892 patent). In pertinent part, the '892 patent discloses FIAC dosages for the treatment of humans of up to 400 mg/m² per day, preferably 120 mg/m² per day. (The recommended dosages are expressed as mg of drug per m² of body surface area.) The '892 patent also teaches that the minimum practical dosage of FIAC is 60 mg/m² per day and that below this amount, "the effects of the drug is [sic] too small." (See, column 5, line 53 of the specification of U.S. Pat. No. 4,666,892.) The '892 patent reference also notes that FIAU is a metabolite of FIAC, and that FIAU is to be used in the same dosage ranges as FIAC. Lastly, it is also mentioned in this patent reference that the sodium salt of FIAU can be prepared, thereby increasing the water-solubility of the nucleoside.

It has been estimated that the average 50 kg female person has a body surface area of about 1.2 to about 1.6 m², with a mean value of about 1.45 m², and that a typical male person weighing about 70 kg correspondingly has a body surface area of about 1.6 to about 1.9 m², with a mean value of about 1.8 m². Taking these mean values for the body surface area, the '892 patent thus teaches that the minimum effective antiviral dose of FIAC or FIAU cannot fall below about 1.7–1.8 mg/kg/day. Indeed, the preferred daily dose, according to this patent reference is about 3.1–3.5 mg/kg. Hence, based on the general teachings of the art, one would not expect to observe antiviral activity against HBV at dosages below those described above.

Interferon-Alpha Against HBV Infection

Currently only interferon-alpha has been shown to be therapeutically useful in the treatment of hepatitis B. However, only a minority of patients respond to interferon. Furthermore, treatment by subcutaneous injection must continue for months, and toxicity at effective doses is substantial. (Alexander, G. J. M. et al. *Lancet* 1987, 1:66–68; Hoofnagle, J. H. et al. *Gastroenterology* 1988, 95:1318–1325; Perrillo, R. et al. *N. Engl. J. Med.* 1990, 323:295–301; Renault, P. F. and Hoofnagle, J. H. *Seminars in Liver Disease* 1989, 9:273–277; Sherlock, S. and Thomas, H. C. Lancet 1985, 2:1343–1346; Scullard, G. H. et al. *Hepatology* 1981, 1:228–232.)

Suppression of levels of HBV DNA or viral DNA polymerase may take weeks of interferon-alpha therapy to be apparent. Results of antiviral therapy in HIV-infected (Novick, D. M. et al. *J. Hepatol.* 1984, 1:29–35) and other immune compromised patients are reported to be worse. (Scullard, G. B. et al. *J. Infect. Dis.* 1981, 143:772–783).

Thus, there remains a very strong need for an effective therapy against infection or disease caused by HBV, particularly in already immune-compromised patients, such as those concurrently infected with HIV. Indeed, pharmaceutical compositions are needed which are not only effective against HBV, as evidenced by the drastic inhibition or reduction of the levels of circulating markers for HBV, but which are effective in maintaining a substantial proportion of such inhibition or reduction for a significant period of time after therapy as been discontinued. Furthermore, orally administrable antiviral compositions with a high level of activity against HBV, with manageable toxicity at effective therapeutic doses, would fill a critical need in current but lacking therapeutic regimens for infection or disease caused by the hepatitis B virus.

SUMMARY OF THE INVENTION

To the great surprise of the applicants, pharmaceutical compositions comprising 1-(2'-deoxy-2'-fluoro-β-D-arabinofuranosyl)-5-iodouracil (FIAU, also known as fialuridine) and a pharmaceutically acceptable carrier have been discovered which are effective at very low doses to decrease rapidly and profoundly the serum levels of circulating markers of HBV replication, such as HBV DNA and HBV DNA polymerase, in human patients, even those concurrently infected with HIV. Moreover, the reduction in HBV DNA or HBV DNA polymerase is substantially maintained post-therapy, as discussed further below, in the patients treated with the compositions of the present invention.

Thus, it is an objective of the present invention to provide a pharmaceutical composition for the treatment of infection or disease caused by the hepatitis B virus which comprises a pharmaceutically acceptable carrier and an amount of FIAU sufficient to provide a low but antivirally effective dosage of FIAU in the range of about 0.05 to about 1 mg/kg-day. Preferably, the amount of FIAU provided falls in the range of about 0.1 to about 0.5 mg/kg-day. The present invention also contemplates a pharmaceutical composition comprising a compound that is a prodrug of FIAU or a compound that is a metabolite of FIAU. In particular, FIAC can be used as a prodrug, in place of FIAU. Likewise, a metabolite of FIAU, 1-(2'-deoxy-2'-fluoro-β-D-arabinofuranosyl)uracil (FAU), can be used to form at least part of the active ingredient of the pharmaceutical antiviral composition of the present invention.

Yet another object of the present invention is to provide a pharmaceutical composition for the treatment of infection or disease caused by the hepatitis B virus which comprises an amount of FIAU, a compound that is a prodrug of FIAU or a compound that is a metabolite of FIAU sufficient to provide a steady state peak plasma concentration of FIAU, its prodrug or metabolite in the range of about 0.1 to about 1 μg/ml and a pharmaceutically acceptable carrier.

In yet another aspect of the present invention pharmaceutical compositions for the treatment of infection or disease caused by the hepatitis B virus are disclosed which comprise FIAU, a compound that is a prodrug of FIAU or a compound that is a metabolite of FIAU and a pharmaceutically acceptable carrier, said compositions containing about 0.25, 0.5, 1, 2 or 5 mg of FIAU, its prodrug or metabolite.

Further objects of the invention include providing compositions effective in a therapeutic regimen against HBV while minimizing or eliminating the side effects associated with the administration of FIAU, its prodrug or metabolite at the high dosages recommended in the prior art.

Also contemplated by the present applicants are methods for the preparation of pharmaceutical antiviral compositions comprising admixing the antivirally active ingredients with a pharmaceutically acceptable carrier. In particular, pharmaceutical compositions in the form of solutions, suspensions, syrups, tablets, caplets or capsules are contemplated.

Methods of treating human patients infected with HBV or suffering from a disease caused by HBV comprising the administration of the compositions of the present invention are likewise contemplated. Modes of administration include oral or parenteral administration. Further, the period of treatment is variable, generally lasting about 7 to about 28 days, preferably about 14 days.

Thus, these and other objects of the present invention will become apparent to those skilled in the art from a reading of the instant disclosure.

DETAILED DESCRIPTION OF THE INVENTION

Antiviral Formulations

Figure 1:
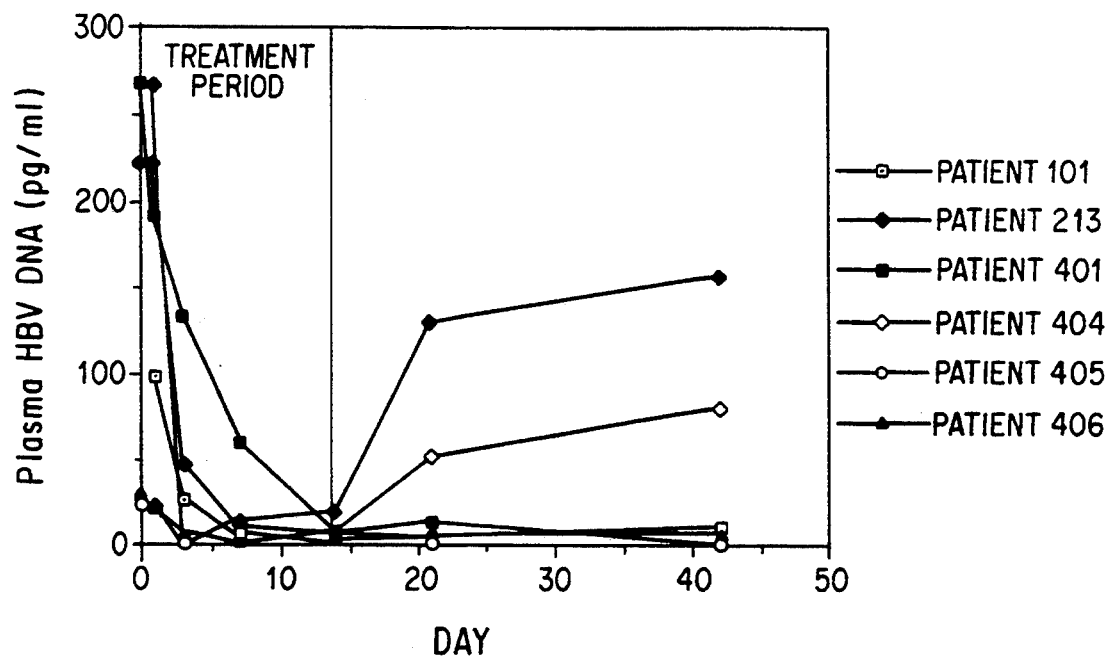
FIG. 1 shows the effect of FIAU on the amount of HBV DNA in plasma of patients.

Because FIAC and FIAU are stable in an acid environment, such as is found in the human stomach, they can be formulated readily using pharmaceutically acceptable carriers well known in the art, with or without pH buffers, into dosages suitable for oral administration. Such carriers enable FIAU, its prodrug or metabolite to be formulated as tablets, pills, capsules, liquids, gels, syrups, suspensions and the like, for oral ingestion by a patient to be treated for infection or disease caused by hepatitis B. With proper choice of carrier and suitable manufacturing practice, the compositions of the present invention, in particular, those formulated as solutions, may also be administered parenterally, such as by intravenous, subcutaneous or intramuscular injection.

Pharmaceutical compositions within the scope of the present invention include compositions wherein the active ingredient is contained in an effective amount to achieve its intended purpose. Determination of the effective amounts is well within the capability of those skilled in the art, especially in light of the detailed disclosure provided herein.

In addition to the pyrimidine nucleosides of the present invention, these pharmaceutical compositions may contain suitable pharmaceutically acceptable carriers comprising excipients and auxiliaries which facilitate processing of the active compounds into preparations which can be used pharmaceutically. Preferably, the preparations are formulated for oral administration, and are in the form of tablets, dragees, and capsules. Alternatively, the preparations may be administered rectally, such as in the form of suppositories. Alternatively, solutions may be prepared for oral or parenterally. The compositions of the present invention contain from about 0.1 to about 5 mg of FIAU, its prodrug or metabolite, with the balance comprising the components of the pharmaceutical carrier.

The pharmaceutical compositions of the present invention may be manufactured in a manner that is itself known, e.g., by means of conventional mixing, granulating, dragee-making, dissolving, or lyophilizing processes. Thus, pharmaceutical preparations for oral use can be obtained by combining the active compounds with solid excipients, optionally grinding a resulting mixture, and processing the mixture of granules, after adding suitable auxiliaries, if desired, to obtain tablets or dragee cores.

Suitable excipients are, in particular, fillers such as sugars, such as lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Additional auxiliaries that can be used include, but are not limited to, flow-regulating agents and lubricants, such as silica, talc, stearic acid or salts thereof such as magnesium or calcium stearate, and/or polyethylene glycol. Dragee cores are provided with suitable coatings. For this purpose, concentrated sugar solutions may be used, which may optionally contain gum arabic, talc, polyvinyl pyrrolidone, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Other pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols or higher alkanols. In addition, it is also possible to use gelatin rectal capsules that consist of a combination of the active compounds with a base. Possible base materials include, for example, liquid triglycerides, polyethylene glycols, or paraffin hydrocarbons.

One of the preferred formulations of the compositions of the present invention are flavored syrups that contain about 1 to about 10 mg of active substance per ml of syrup. Thus, in a particular embodiment of the present invention, a flavored syrup comprises about 0.1 to about 1 percent by weight of the syrup (wt %) FIAU or FIAC, about 5–50 wt % purified water USP, about 5–50 wt % glycerin USP, about 5–50 wt % alcohol USP, about 5–50 wt % propylene glycol USP. In addition, the syrup also comprises about 0.0001–0.01 wt % of a coloring agent or combinations thereof, such as FD&C Red #40, FD&C Yellow #5 or FD&C Blue #1, about 0.01–0.1 wt % flavoring agents, such as artificial or natural Gran Marnier, orange, cherry, vanilla, strawberry, raspberry, lemon or chocolate flavor. Moreover, commercially available syrup additives, such as Syrup NF qs ad or Maltitol syrup, are preferably present at about 0.01 to about 0.1 wt %.

As mentioned, previously above, pharmaceutical preparations may also be prepared for parenteral administration. Suitable formulation for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers.

Specific examples of the pharmaceutical compositions of the present invention are presented in further detail in the Examples Section of the present specification.

Dosage Regimens

The precise dosage amounts to be administered will be determined by routine experimentation. In general, however, the dosage amounts will be comparable or less than those already disclosed in the clinical studies described herein. In particular, low dosage regimens are preferred which range from about 0.05 to about 1 mg/kg-day. Most preferably, dosage levels of about 0.1 to about 0.5 mg/kg-day are to be administered continuously for about two weeks to immune-compromised patients suffering concurrently from chronic hepatitis B. For immune-competent (e.g., non-HIV-positive) HBV-infected patients, preferred dosage regimens of about 0.05 to about 0.5 mg/kg-day for about two weeks are anticipated.

Alternatively, dosage levels of active ingredient are administered to HBV-infected patients to achieve a steady state antivirally effective peak plasma concentration of FIAU, its prodrug or metabolite in the range of about 0.1 to about 1 µg/ml. Indeed, it is anticipated that the active intracellular form of FIAU (or, possibly, also its metabolite, such as FAU) is the triphosphate. Hence, the present invention contemplates compositions that, when administered at certain dosage levels, provide or maintain intracellular amounts of the triphosphate form of the active ingredient which are effective to inhibit the hepatitis B virus. Such inhibition is demonstrated by the reduction of, preferably continued post-therapy suppression of, baseline entry levels of HBV DNA or HBV DNA polymerase.

Summary of Results of Clinical Studies With Immune-Compromised Patients at Daily 1 Milligram Per Kilogram Dosage of FIAU Tolerance to the oral formulation of FIAU was evaluated in relatively healthy HIV-infected patients with Karnofsky performance scores $\geq 80$ and $\geq 200$ $CD_4$ cells/mm$^3$. Sequential cohorts of ten patients were evaluated in an open and uncontrolled study design. Consecutive cohorts were scheduled to receive increasing doses of FIAU syrup (10 mg/ml) TID for 14 days starting at 1.0 mg/kg-day. Tolerance was determined with concurrent anti-emetic therapy (prochlorperazine or metoclopramide hydrochloride) as necessary for each patient.

Cohorts of five HIV-infected patients with chronic hepatitis B were studied at the tolerated doses. Plasma levels of FIAU and its major deiodinated metabolite FAU were determined two hours after dosing (peak levels) and just prior to dosing (trough levels) following the initial dose of FIAU and again on Days 3, 7, and 14 in order to make estimates of pharmacokinetic parameters including accumulation of drug or principal metabolite.

Oral FIAU was adequately tolerated by the initial ten patients without chronic hepatitis B dosed at 1.0 mg/kg-day. Nausea and headache were the most commonly reported symptoms. Eight patients experienced mild to moderate nausea and four required anti-emetic therapy. Five patients complained of mild to moderate headache. Eight of the patients completed their scheduled therapy while two patients withdrew prematurely. One patient withdrew after a week of therapy due to moderate nausea. A second patient withdrew on the tenth day of therapy with severe fatigue, moderate nausea and headache.

A slight, but not significant (p=0.0746), decrease in WBC count from an average of 5,480 to 4,920 cells/mm$^3$ was noted over the course of therapy, along with minor, but significant (p$\leq$0.02) increases in liver enzymes. The average AST and ALT values increased from 23.4 to 29.6 and from 27.1 to 42.3, respectively, over the course of therapy. Peak and trough levels of FIAU were quite consistent between patients and remained stable after Day 3. Peak values averaged approximately 1 µg/ml at steady state, while trough values were typically under 0.2 µg/ml. FAU values rarely exceeded 0.15 µg/ml and showed less variation between peak and trough. Neither compound tended to accumulate over the treatment period.

Three similar patients were dosed at 1.7 mg/kg-day as a part of the next sequential dose cohort. All three discontinued the study after two to eight days due to severe fatigue that was accompanied by moderate nausea in all and mild to moderate vomiting in two. Symptoms were unaccompanied by any substantial changes in hematology or blood chemistry values.

Six patients with chronic hepatitis B virus (HBV) infection in addition to their HIV infection were then dosed at 1.0 mg/kg-day for 14 days. Nausea was the most commonly reported symptom. Four patients reported mild to moderate nausea and all four requested anti-emetic therapy. All six patients completed the full course of therapy.

Patterns of hematologic toxicity were similar to those seen in the non-HBV-infected patients, although in this case the decrease in WBC from an average of 4,690 to 3,430 was significant (p=0.0085), while the increases in liver enzymes were not (p>0.1). Baseline AST and ALT values were approximately twice those of the non-HBV-infected group. One patient experienced an episode of myositis that developed just after dosing was completed. The peak and trough values of FIAU and FAU were not different from those found in the HIV-infected patients without chronic hepatitis B.

Dosing with FIAU resulted in rapid and profound decreases in plasma levels of HBV DNA polymerase and HBV DNA. Reductions of 70% or more were recorded in plasma levels of HBV DNA after two days of therapy. By the end of therapy, more than a 90% reduction was seen in five of the six patients. Four weeks after therapy ceased, three of the patients had a partial rebound in plasma HBV DNA levels not exceeding 50% of baseline levels. Two showed a complete clearing of HBV DNA from the plasma and the third had more than 90% suppression.

In an important downward dose ranging design that will reveal the minimal active dose for viral DNA suppression, patients chronically infected with HBV are enrolled in a treatment regime in which daily doses of FIAU at 0.05, 0.1 and 0.5 mg/kg are administered for up to about 28 consecutive days, preferably about two weeks. Preliminary results indicate that undesired side effects are minimized, if not eliminated, at such lower but antivirally effective dosages.

A summary of the results of clinical studies with immune-compromised patients at daily submilligram per kilogram dosage levels of FIAU is presented below, in Section 6 of the instant specification.

EXAMPLE

Clinical Studies With Immune-Compromised Patients

It has been demonstrated by clinical studies that the compositions of the present invention are effective at a daily low dose of about 0.05 to about 1.0 mg/kg, preferably about 0.1 to about 0.5 mg/kg, to reduce drastically the serum levels of HBV DNA or HBV DNA polymerase. In one case, the use of the composition of the present invention even resulted in the disappearance of the circulating envelope antigen. Of particular significance, the compositions of the present invention were found to be effective in HBV-infected patients who are also infected with HIV and, thus, more difficult to treat.

Moreover, in the low antiviral dosages discovered in the present invention, virtually all side effects observed at high dosages, such as nausea, muscle fatigue, or gastrointestinal irritation, are eliminated.

Results of Initial Studies

This study showed that the maximum tolerated dose of oral FIAU is at least 1.0 but less than 1.7 mg/kg-day in the HIV-infected population tested, and that a dose of 1.0 mg/kg-day has a rapid, consistent, profound and prolonged effect on plasma HBV DNA and viral DNA polymerase levels in patients who also have chronic hepatitis B.

Based on these results, the study was amended to increase each HBV cohort to ten patients and to add two additional cohorts of HIV-infected patients with chronic hepatitis B, one at 0.5 mg/kg-day, another at 0.1 mg/kg-day, and yet another at 0.05 mg/kg-day, in an attempt to find the lowest dose producing a reliable and significant effect on plasma HBV DNA levels. Detailed pharmacokinetic evaluations are made in two patients of each dose group in this ongoing downward dose ranging design.

The suppressive effect of FIAU on HBV DNA is more rapid and consistent than that recorded for any compound previously tested in hepatitis B envelope antigen (HBeAg) positive chronic HBV infection. As stated previously, less than half of patients treated with interferon-alpha showed major and sustained decreases in this marker. To obtain these results even in a minority of patients, interferon-alpha therapy must be given for months and toxicity requiring dosage reductions and termination of therapy is common.

Ara-AMP has shown a more consistent effect than interferon. However, rapid rebound of DNA levels to pretreatment levels after 10–28 days of therapy is the norm and continued administration at HBV DNA suppressive doses has proved to be intolerably toxic. It is reasonable to expect that similar to the patients successfully treated with interferon-alpha and in patients who have spontaneous remission of chronic HBV infection, patients exhibiting sustained clearance of plasma HBV DNA after treatment with FIAU will continue to improve. This sustained clearance period is followed by normalization of liver enzymes, disappearance of HBeAg, appearance of anti-HBeAg, and improved liver histology, i.e., remission of inflammatory hepatitis.

Two of the patients in this study showed a transient flare in liver enzymes at the end or shortly after the end of therapy similar to that typically seen in patients that responded to interferon-alpha treatment. One of these two patients lost circulating HBeAg, and follow-up of two others with no or minimal residual plasma HBV DNA continues.

It is significant that these very positive results were obtained in immunologically compromised HIV-infected subjects. Results in immune competent patients are expected to be even better, especially in terms of efficacy and tolerance, because immune competence is thought to be important to eventual viral clearance and because immunological function declines progressively in the HIV-infected population that has so far been studied.

METHODS

Study Design

This study is an open label, uncontrolled trial. Sequential dose groups of ten patients were to be studied for tolerance to 14 days of TID oral dosing with FIAU syrup (10 mg/ml). Tolerated doses could be studied in an additional five patient cohort of chronic hepatitis B patients, who were potentially more at risk of side effects. A month of post-treatment follow-up was provided for the hepatitis cohorts due to the known propensity of this disease to "flare" after therapy.

Although not formally randomized, qualified patients were to be consecutively enrolled without regard to their disease severity, expected tolerance, or potential benefit of the dose being evaluated. Tolerance to a dose was defined as seven or more of the ten patients in a cohort individually meeting predefined tolerance criteria including successful completion of therapy and limits on changes in particular signs, symptoms and laboratory tests. Tolerance was determined with concurrent anti-emetic therapy for those patients requiring it. Criteria and regimens for such therapy were predefined.

When it became apparent that 1.7 mg/kg-day was not tolerated and that 1.0 mg/kg-day was having a profound effect on circulating hepatitis B DNA, a series of protocol amendments were added to the protocol to refocus the study toward examining the effect of FIAU on hepatitis B in more patients, determining the minimal effective dose for hepatitis B DNA suppression and exploring some limited retreatment options for patients whose hepatitis markers rebound during follow-up.

Patients

HIV-infected patients between 13 and 65 years of age with or without a current episode of a chronic herpes group virus infection (HSV, VZV, or CMV) were eligible to participate in the ten patient tolerance cohorts if they had a Karnofsky performance score $\geq 80$ and $\geq 200$ $CD_4$ cells/mm$^3$. Additionally, patients of both sexes must have agreed to use birth control during the study and for three additional months afterward. Patients concurrently taking zidovudine must have been taking the drug for more than six weeks at a dose $\leq 600$ mg/day, and must have had less than a 10% decrease in hematocrit, neutrophils and platelets in the last 30 days. Weight loss was restricted to less than 10% in the past three months and serum CPK was required to be within the normal range.

Additionally, all patients had to have completed the screening tests within four weeks of starting therapy, except for diagnostic HSV, VZV or CMV cultures. Those enrolled into the five patient cohorts of chronic hepatitis B patients had the same entry requirements, except that they had to have a history of chronic hepatitis B and be surface antigen positive. Liver function tests (AST, ALT, GGT, and bilirubin) could be Grade 2 or less at study entry for these patients. Patients receiving pentamidine aerosol for prophylaxis of recurrent Pneumocystis pneumonia could continue on this therapy during the study.

Any serious or unstable medical condition would automatically exclude a patient. Patients could not have a primary or initial infection with HSV, VZV or HBV, or evidence of CMV end organ disease, e.g., retinitis, hepatitis, gastroenteritis. Patients were excluded if they had evidence of HIV wasting syndrome (involuntary weight loss $\geq 10\%$ and/or chronic diarrhea or weakness and documented fever for at least 30 days), idiopathic thrombocytopenic purpura (persistent platelet counts $< 100,000$/mm$^3$ for three or more months), clinical or x-ray evidence of bronchitis, pneumonitis, pulmonary edema, effusions, or suspected active tuberculosis. Use within four weeks of study entry of ganciclovir, foscarnet, interferon or any other drug with putative anti-viral activity (except zidovudine) or immunostimulating properties would exclude a patient, as would use of acyclovir within one week of study entry.

Patients were excluded for hemoglobin $< 9.5$ g/dl, hematocrit $<34$, neutrophils $<1500$/mm$^3$, or platelets $<100,000$/mm$^3$. Total bilirubin $>1.5$ times the upper limit of the normal range would exclude a patient, as would BUN, AST or ALT $>2.5$ times, except that for the chronic HBV patients these limits could be $>2.5$ for bilirubin and $>5$ times for AST, ALT, and GGT. Patients were requested to avoid heavy exercise for 24 hours before any laboratory tests.

Investigational Procedures

Concurrent Anti-Emetic Therapy

Patients experiencing sustained nausea or two or more episodes of vomiting were eligible for concurrent anti-emetic therapy as defined below:
Reglan ® 10 mg, p.o., Q6H, prn or
Compazine ® 10 mg, p.o., Q6H, prn, or 25 mg, p.r. Q12H, prn or
Trilafon ® 4 mg, p.o., Q6H, prn.

Efficacy Evaluations

Effects on hepatitis were evaluated principally by changes in HBV DNA and viral DNA polymerase. Secondary markers were surface antigen and e antigen. The hepatitis tests were done at Baseline and on Days 3, 7, 14, 21 (7 days post-treatment) and 42 (28 days post-treatment).

Safety Evaluations

Patients were evaluated clinically at the screening visit, and on Days 1, 3, 7, 10, and 14. The hepatitis patients were additionally evaluated on Days 21 and 42. The blood chemistry and urinalysis tests were repeated additionally on Days 2 and 5.

Clinical evaluations consisted of a physical exam, which included a test of lower extremity muscle strength, medical history, systems review, grading of non-laboratory signs and symptoms of toxicity, and listing of concomitant medications. Additionally, at visits with clinical evaluations after Day 1, any adverse experiences were recorded.

At the screening visit a chest x-ray, electrocardiogram (ECG), HIV test, T cell profile ($CD_4$ and $CD_8$ counts), serum biochemistry, hematology, urinalysis and stool guaiac tests were obtained in addition to the clinical evaluation. Hematology tests consisted of hemoglobin, hematocrit, RBC, WBC and differential, platelet, reticulocyte count, MCV, MCHC and MCH. Urinalysis tests consisted of color, appearance, pH, specific gravity, bilirubin, protein, glucose, myoglobin, RBCs, WBCs, casts, crystals and bacteria. Serum biochemistry tests consisted of creatinine, uric acid, BUN, total bilirubin, AST, ALT, alkaline phosphatase, LDH, CPK, CPK-MB, glucose, total protein, albumin, globulin, calcium, phosphorus, potassium, sodium, chloride, bicarbonate and aldolase.

The Baseline visit (Day 1) consisted of repeating the clinical evaluation, hematology, serum biochemistry, urinalysis, and stool guaiac tests, and T cell profile. Additionally at Baseline, archive plasma samples were taken. Plasma samples were taken two hours after each patient's first dose of FIAU (peak) and right before the second dose (trough). Thereafter, on Days 3, 7 and 14 additional peak and trough samples were obtained by taking the trough sample just before a patient took a dose of FIAU and the peak sample two hours later. These samples were analyzed by HPLC for levels of FIAU and FAU as low as 0.05 $\mu$g/ml for either compound.

The Day 3 safety profile consisted of the clinical evaluation, hematology, serum biochemistry, urinalysis, stool guaiac tests and plasma samples for peak and trough levels of FIAU and its major metabolite FAU. On Day 7 patients underwent clinical evaluation, an ECG, peak and trough serum samples, T cell profile, and hematology, serum biochemistry, urinalysis, and stool guaiac tests. A clinical evaluation, hematology, serum biochemistry, and urinalysis tests were done on Day 10. These were repeated for the Day 14 evaluation with the addition of an ECG, T cell profile, stool guaiac, and peak and trough plasma samples. The post-treatment evaluations of the hepatitis patients on Days 21 and 42 consisted of a clinical evaluation and serum biochemistry tests.

Clinical Supplies and Dosing

Eight-ounce amber bottles containing 240 ml of FIAU syrup (10 mg/ml), as described further in the Examples Section of the present specification, were used in the investigation. Additionally, investigators were supplied with 10 ml oral dosing syringes, adaptor caps for the bottles of FIAU and tapes for each syringe to mark the dose to be taken. Two week stability of the syrup in the oral dosing syringes has been verified.

Each bottle of medication was identified with the patient's initials, patient number, dose group to which the patient belonged, date of dispensing, and the volume of syrup to be taken TID. Patients were instructed on the proper use of the oral dosing syringes and told to take the medication every eight hours at least one hour prior to or three hours following a meal.

Statistical Methods

Due to the uncontrolled and non-randomized nature of the study, descriptive summary statistics were the primary means of analysis. The sequential nature of the study design and non-random assignment of patients to dose groups precludes true validity for before and after analyses of variables or group comparison tests between doses. Nevertheless, such tests can be useful in determining areas of potential effectiveness or concern for safety that would need to be addressed in a more rigorous fashion in a follow-up study.

With this in mind, before and after analyses of parametric data were done using paired t-tests. Two tailed tests, with alpha at 0.05 were used for all inferential analyses. For arbitrary scores and other ordinal non-parametric variables the Wilcoxon matched pairs signed rank test was used. Proportions were evaluated using the Chi-squared test corrected for continuity or the Fisher exact test.

RESULTS

Study Population

A total of 20 patients have been studied. None of the non-hepatitis patients presented at the Baseline visit with an active episode of a herpes group virus infection. Therefore, all of these patients provided only tolerance data. Since all three non-hepatitis patients enrolled at 1.7 mg/kg-day dropped from the study due to severe fatigue between one and seven days after starting therapy, this dose was considered not tolerated and no hepatitis patients were enrolled at this higher dose.

Of the 13 "tolerance" patients, e.g., non-hepatitis patients, enrolled, all received the study drug and all are included in the safety analysis. One of the hepatitis patients (#402) was found to have an elevated Baseline CPK value. He had received a single dose of the study drug, and has, therefore, been included in the safety analysis, but excluded from the efficacy analysis. All of the remaining hepatitis patients had sufficient baseline levels of HBV DNA (>20 pg/ml) and viral DNA polymerase (>300 cpm) in their serum to be useful for determining changes associated with FIAU dosing and all completed the full two weeks of dosing. Therefore, the remaining six hepatitis patients were included in both the safety and efficacy analyses.

Three patients out of a total of 17 (HBV and non-HBV) failed to complete two weeks of dosing at 1.0 mg/kg-day, two due to adverse experiences probably or possibly related to treatment with FIAU. The third patient was discontinued after a single dose of FIAU due to an abnormal baseline CPK value. The two therapy limiting adverse experiences were moderate nausea (Patient 206) and severe fatigue accompanied by moderate nausea and headache (Patient 210).

The three "tolerance" patients enrolled into the 1.7 mg/kg-day dose group all discontinued therapy within 2 to 8 days due primarily to severe fatigue. All were Caucasian and ranged in age from 28 to 39 years of age. Two were male, one female. Baseline $CD_4$ counts of the three patients (numbers 211, 212 and 214) were 442, 793, and 1119, respectively, and none were taking anti-retroviral drugs. One patient (number 212) had grade 1 fatigue at both screening and baseline visits; the others were without symptoms.

Hematological, clinical blood chemistry, and urine parameters were within normal limits at Screen and Baseline for each patient, and did not move outside the normal range in any subsequent examination.

Demographic Characteristics

With one exception, the patients were all males and were between the ages of 25 and 47. Two patients were black and the rest white. The baseline weights of the males ranged from 58.8 to 98.5 kg, while the female patient weighted 56.5 kg. Baseline $CD_4$ counts ranged from 343 to 1190, with a median value of 681.5. Comparison of the baseline demographic, laboratory and non-laboratory toxicity data of the patients between the study centers and dose cohorts revealed no clinically significant differences. The hepatitis B cohort differed from the "tolerance" cohorts in having over twice the average baseline levels of liver enzymes (AST: 54.7 vs. 23.7; p=0.013 and ALT: 69.8 vs. 27.1; p=0.041 via group comparison T tests), although overlap in values between the groups was apparent.

Efficacy Results

Figure 2:
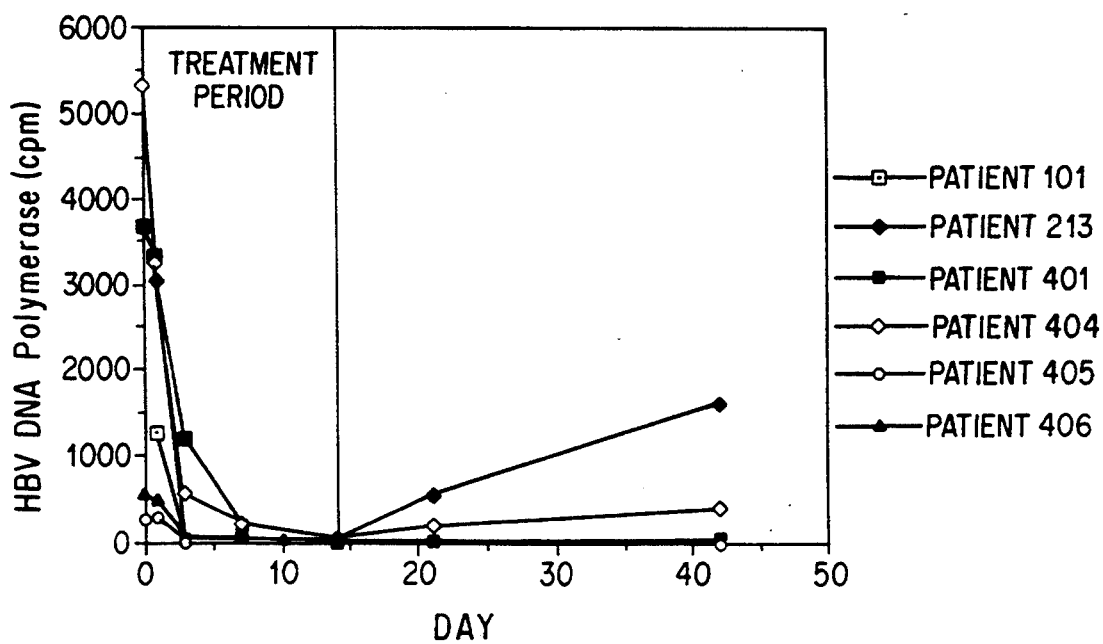
FIG. 2 shows the effect of FIAU on plasma HBV DNA polymerase levels in patients.

As noted above, six of the seven hepatitis patients provided efficacy data, all dosed at 1.0 mg/kg-day. FIAU had an immediate and profound effect on the amounts of HBV DNA (FIG. 1) and viral DNA polymerase (FIG. 2) in the patients' plasma.

Figure 3:
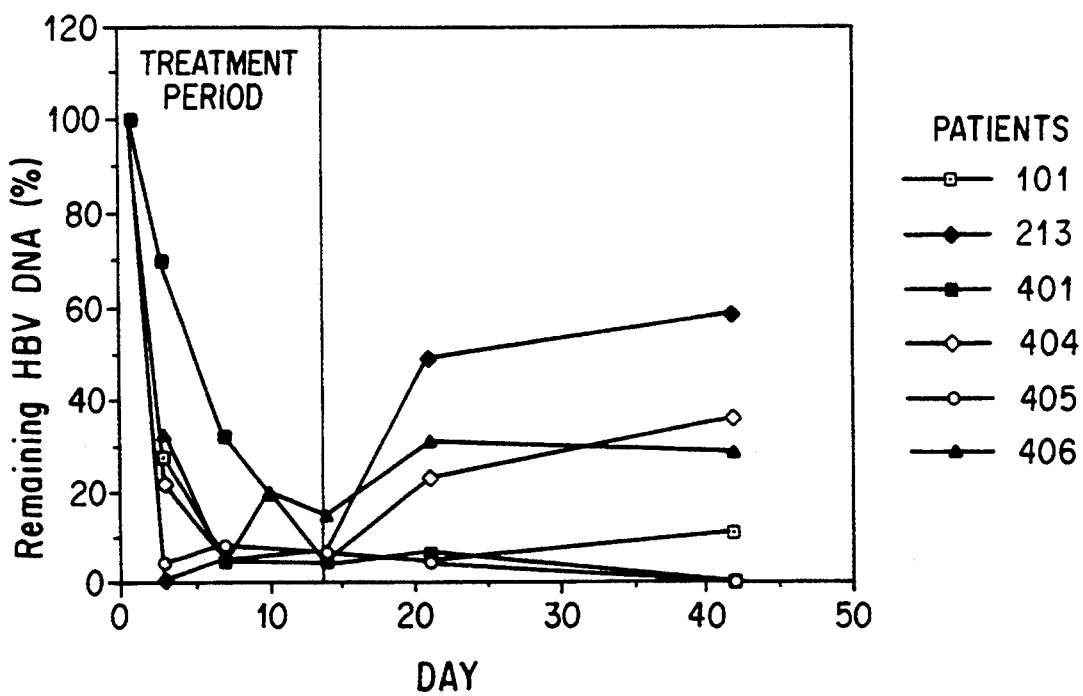
FIGS. 3 and 4 shows the effect of FIAU on the amounts of HBV DNA in plasma of patients.
Figure 4:
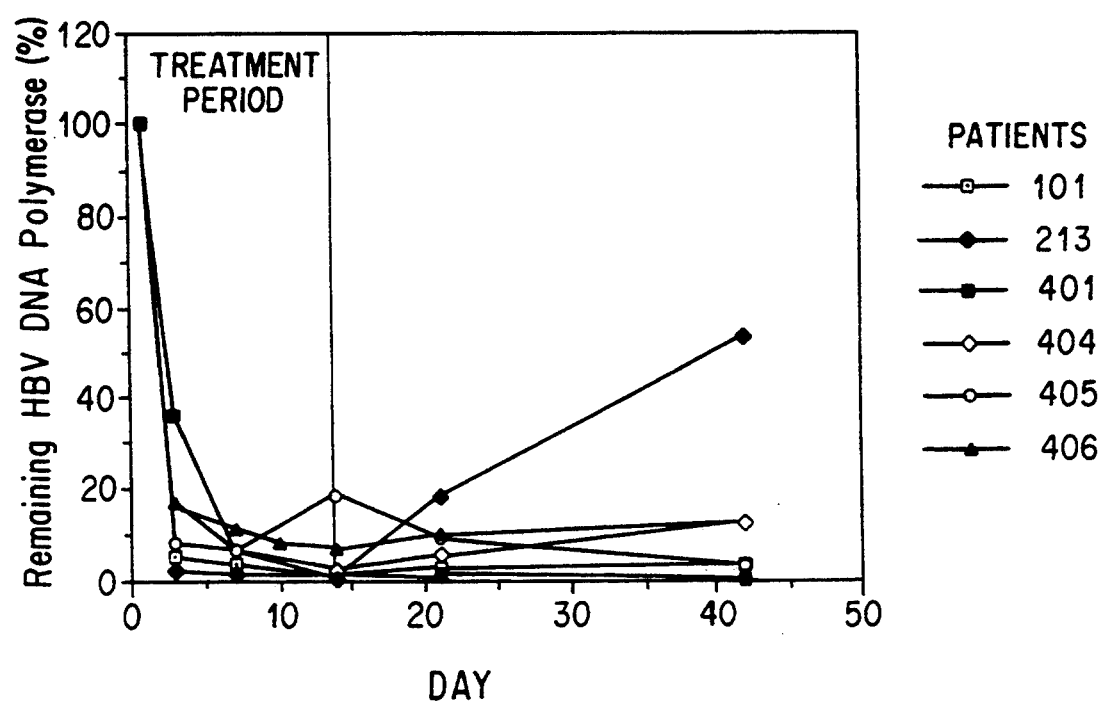

Major decreases, averaging over 70% for HBV DNA, were seen between Baseline (Day 1) and Day 3, i.e., after two days of dosing. This type of decrease was even seen in Patient 401, who had received only the single large dose of FIAU on his first day of treatment. By the end of therapy, five of the six patients had more than 90% reduction in the amount of HBV DNA in their plasma with a corresponding reduction in the values of viral DNA polymerase (FIGS. 3 and 4).

Figure 5:
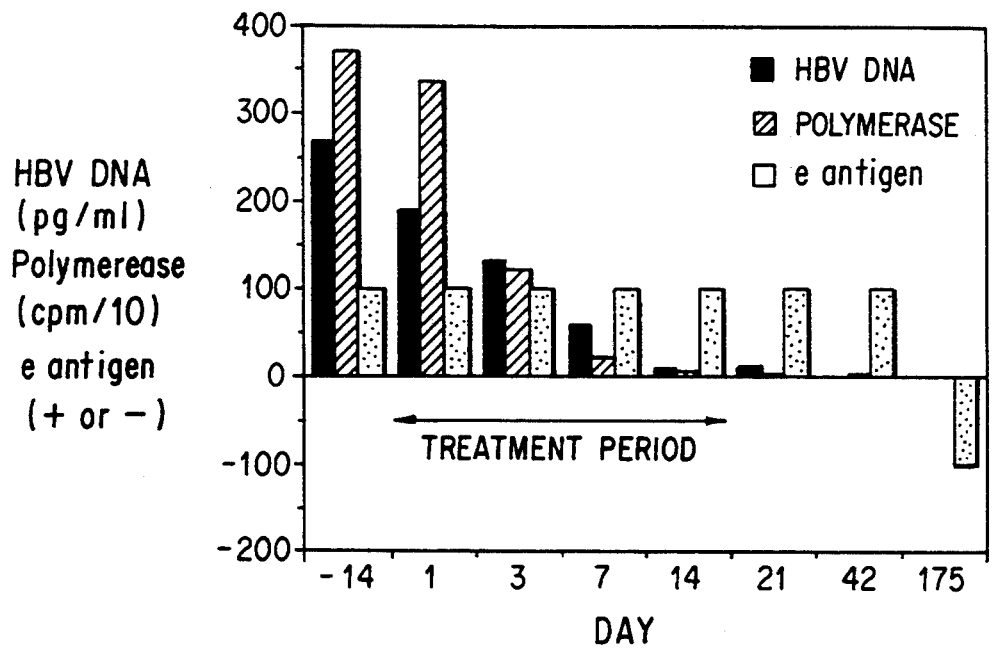
FIG. 5 shows changes in hepatitis markers in a patient treated with FIAU.
Figure 6:
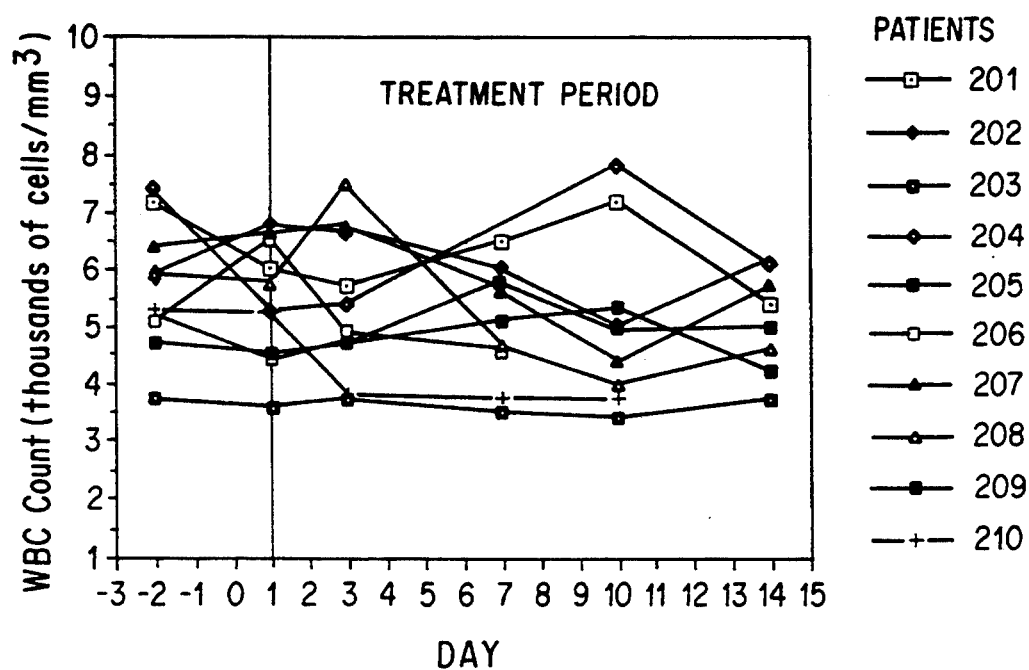
FIG. 6 shows the effect of FIAU on the WBC Count in non-hepatitis patients.
Figure 7:
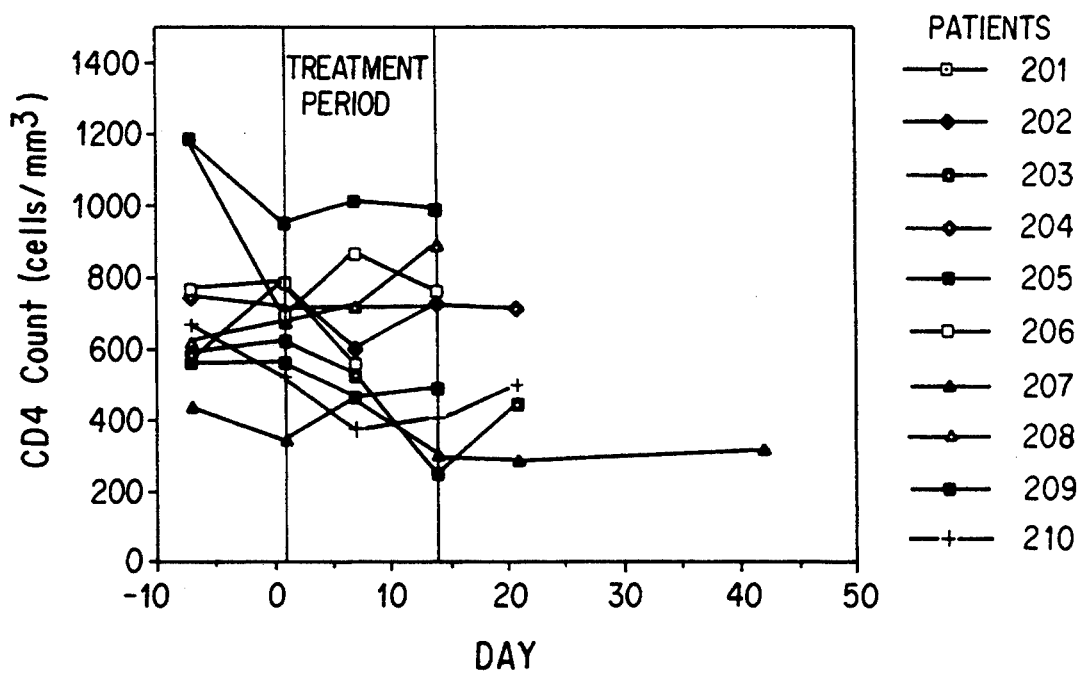
FIG. 7 shows the effect of FIAU on the CD4 Count in non-hepatitis patients.
Figure 8:
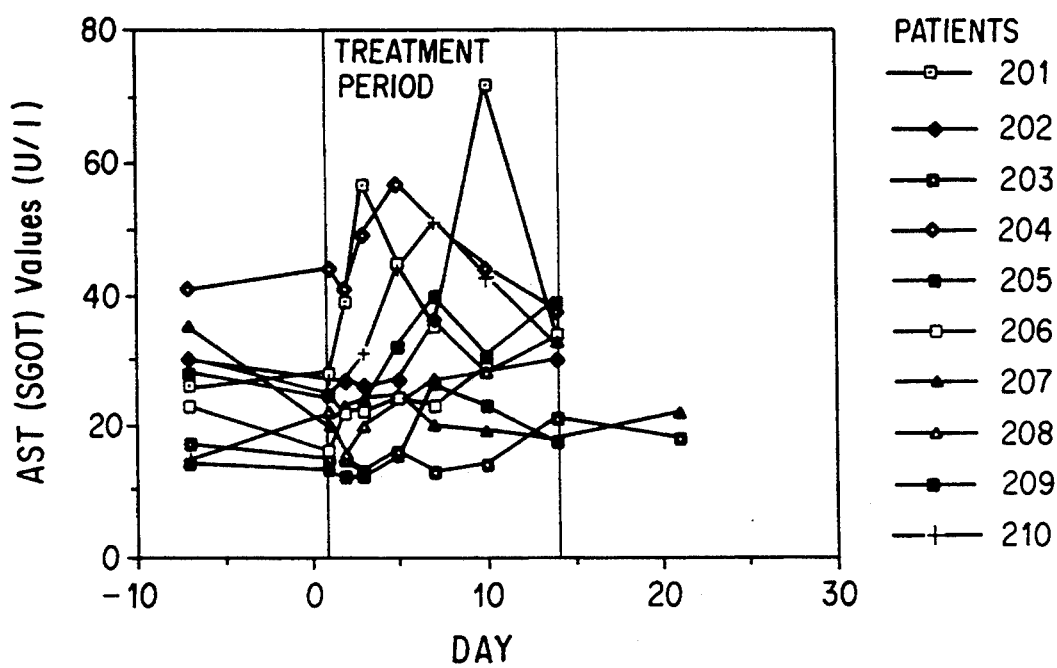
FIG. 8 shows the effect of FIAU on the AST Values of non-hepatitis patients.
Figure 9:
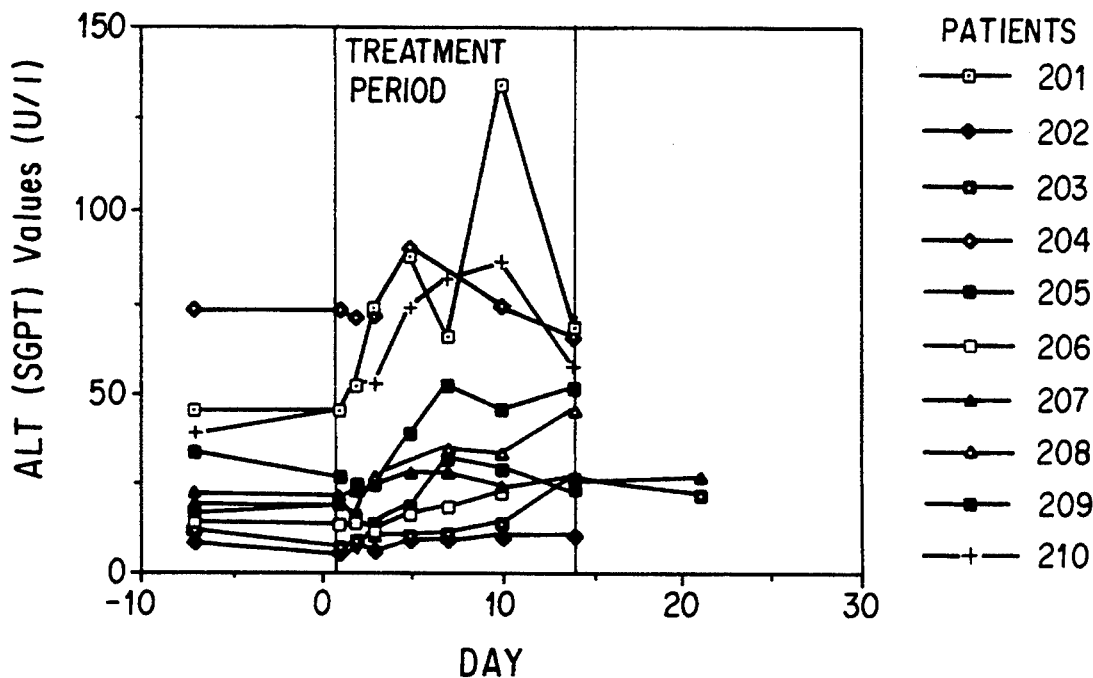
FIG. 9 shows the effect of FIAU on the ALT Values in non-hepatitis patients.

Suppression of both HBV DNA and viral DNA polymerase continued throughout the four weeks of post-treatment follow-up. Three of the patients had >90% suppression of HBV DNA throughout follow-up and two of these became totally negative for this parameter. Three of the six rebounded during the follow-up period, but only to between approximately 25 to 50% of their baseline values. Surface antigen and e antigen have remained positive in all patients to date, with one reported seroreversion of e antigen in Patient 401 approximately 23 weeks post-treatment. The changes in the hepatitis markers with time for this patient are shown in FIG. 5.

Safety Results

Oral FIAU was adequately tolerated at 1.0 mg/kg-day. Of the ten non-hepatitis patients eight completed dosing with no major untoward effects, while six of the seven hepatitis patients completed dosing with the one drop-out in this group being due to an elevated Baseline CPK value. One hepatitis patient (Patient 101) additionally developed severe myositis after dosing had been completed, which the investigator thought was probably related to FIAU. This patient subsequently recovered from his myositis. His biochemical abnormalities resolved within several weeks, while his myalgias required several additional months and resolved concurrently with a reduction in the patient's daily dose of AZT.

The chronic hepatitis B patients tolerated FIAU similarly to those without hepatitis, except that substantial spikes in liver enzymes were noted in two of the hepatitis patients, one near the end of therapy (Patient 401) and the other at the end of the month of post-treatment follow-up (Patient 406). Nausea, headache, fatigue, weakness and dizziness were relatively common. Slight to moderate increases in liver enzymes over the course of dosing and minor decreases in leucocytes were the principal laboratory findings.

Of the ten non-hepatitis patients dosed at 1.0 mg/kg-day, eight experienced mild to moderate nausea and four required anti-emetic therapy. Five complained of mild to moderate headache. A slight, but not significant ($p=0.0746$), decrease in leukocytes from an average of 5,480 to 4,920 cells/mm$^3$ over the course of therapy was noted. Neutrophils and lymphocytes each decreased about 300 cells/mm$^3$ and neither decrease was significant ($p>0.07$). CD$_4$ levels tended to parallel these changes with a non-significant average loss of 64 cells/mm$^3$. Minor, but significant ($p\leq 0.02$) increases in liver enzymes during therapy were noted. The average AST values increased from 23.4 to 29.6 and ALT increased from 27.1 to 42.3. The timeline changes in these parameters are shown in FIGS. 6–9.

Any adverse side effects observed at the 1.0 mg/kg-day dosage level are to alleviated, if not completely eliminated, in the lower dose regimes (i.e., at dosages of 0.05, 0.1 and 0.5 mg/kg-day FIAU, its prodrug or metabolite).

Of the seven hepatitis patients dosed at 1.0 mg/kg-day, one (Patient 402) was dropped immediately after his initial dose when it was reported that he had had an elevated Baseline CPK value. This patient had no immediate symptomatology associated with his single dose of FIAU and no further follow-up was performed on this patient. The remaining six hepatitis patients all completed the 14 days of therapy with no untoward effects. Nausea was the most commonly reported symptom. Four patients reported mild to moderate nausea and all requested anti-emetic Compazine ® therapy.

Figure 10:
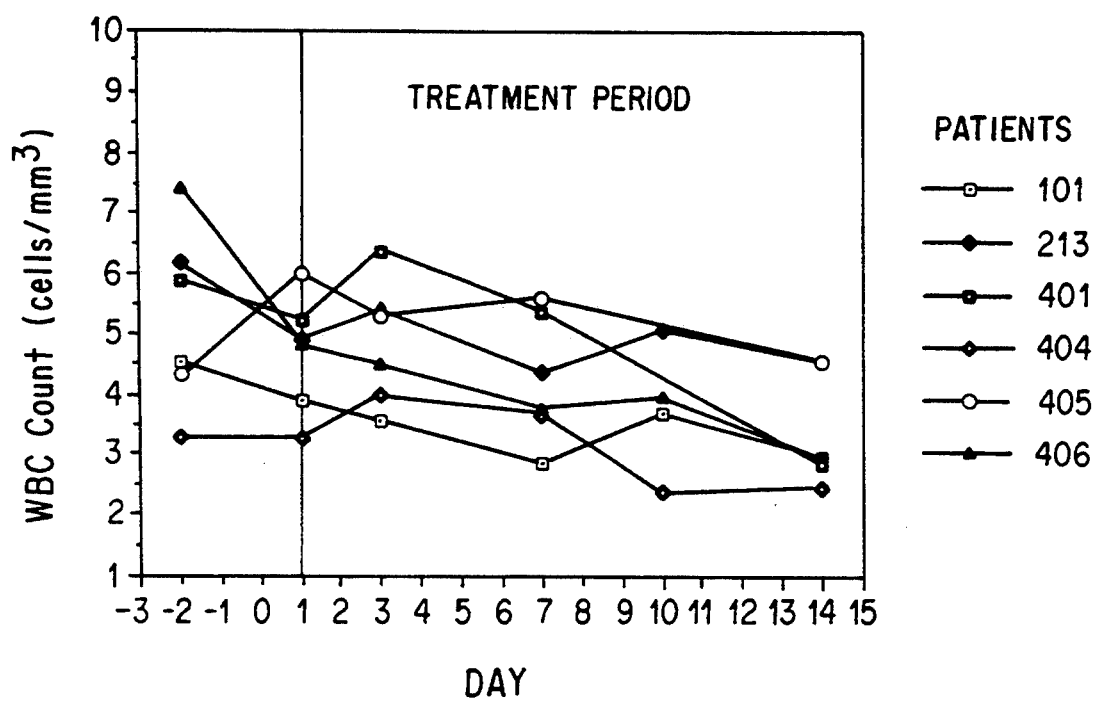
FIG. 10 shows the effect of FIAU on the WBC counts of hepatitis patients.
Figure 11:
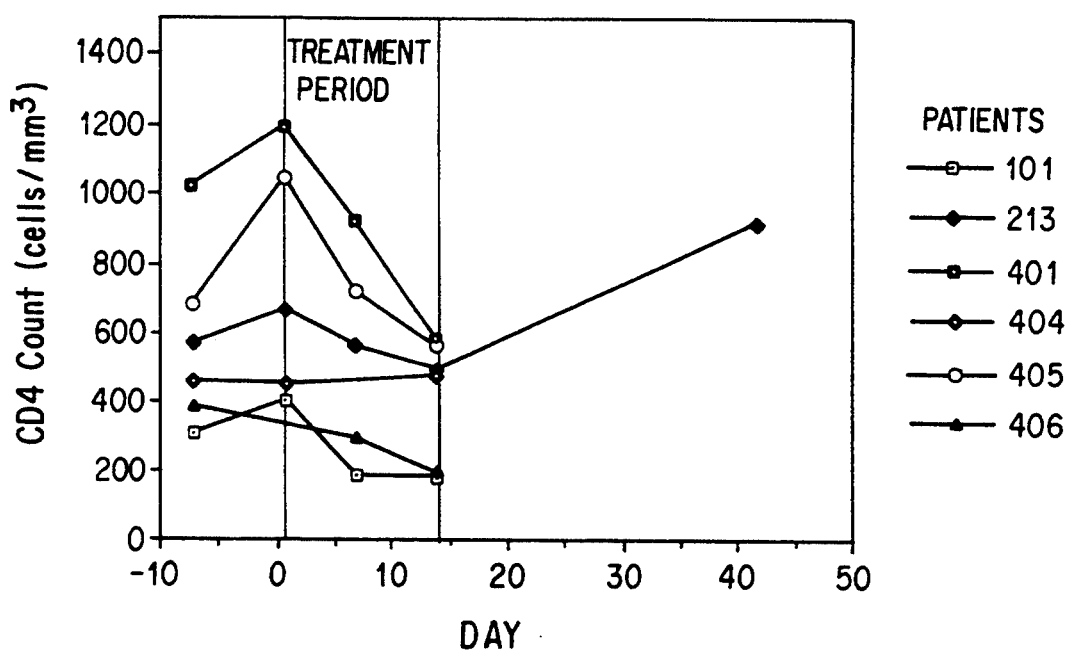
FIG. 11 shows the effect of FIAU on the CD4 counts of hepatitis patients.

Patterns of hematologic toxicity were similar to those seen in the non-HBV-infected patients, although in this case the decrease in WBC (FIG. 10) from an average of 4,690 to 3,430 was significant ($p=0.0085$). Neutrophils showed an average drop of approximately 300 cell/mm$^3$ that was not significant and nearly identical to the non-hepatitis patients. Lymphocytes, however dropped over twice this amount (on average 750 cells/mm$^3$) and this 39% decrease was highly significant ($p=0.00125$). CD$_4$ cells (FIG. 11) dropped in parallel to the total lymphocytes. The average CD$_4$ count was 691 at Baseline, 415 at Day 14, a 40% decrease, that was also significant ($p=0.03$).

Figure 12:
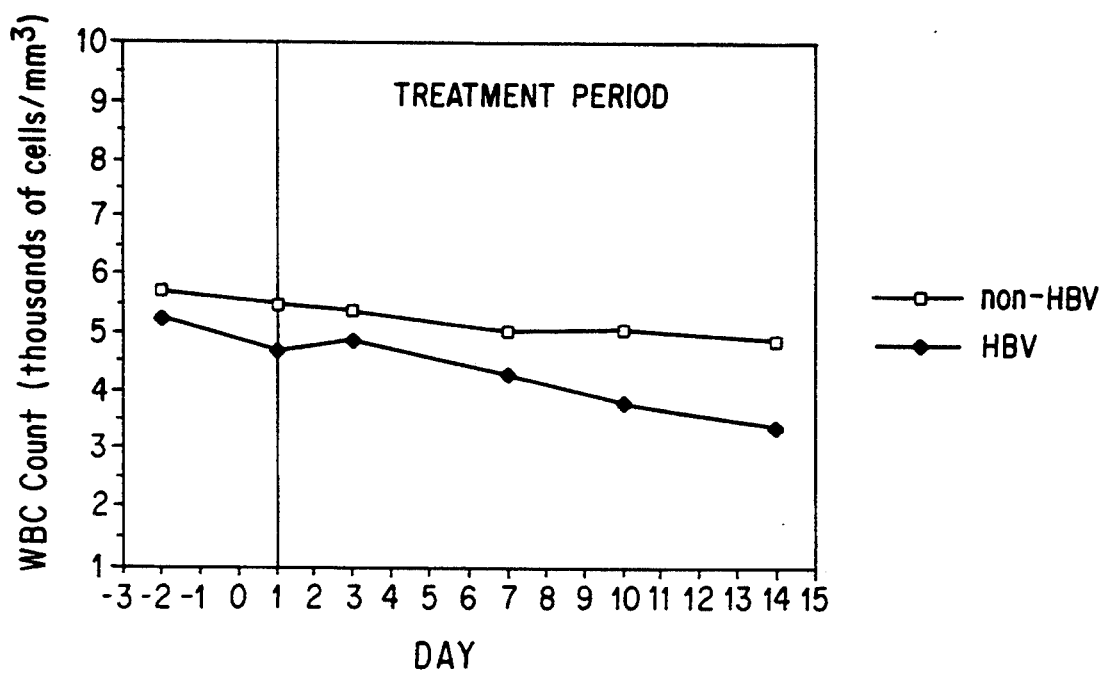
FIG. 12 contrasts the mean WBC counts for the non-hepatitis and hepatitis patients.
Figure 13:
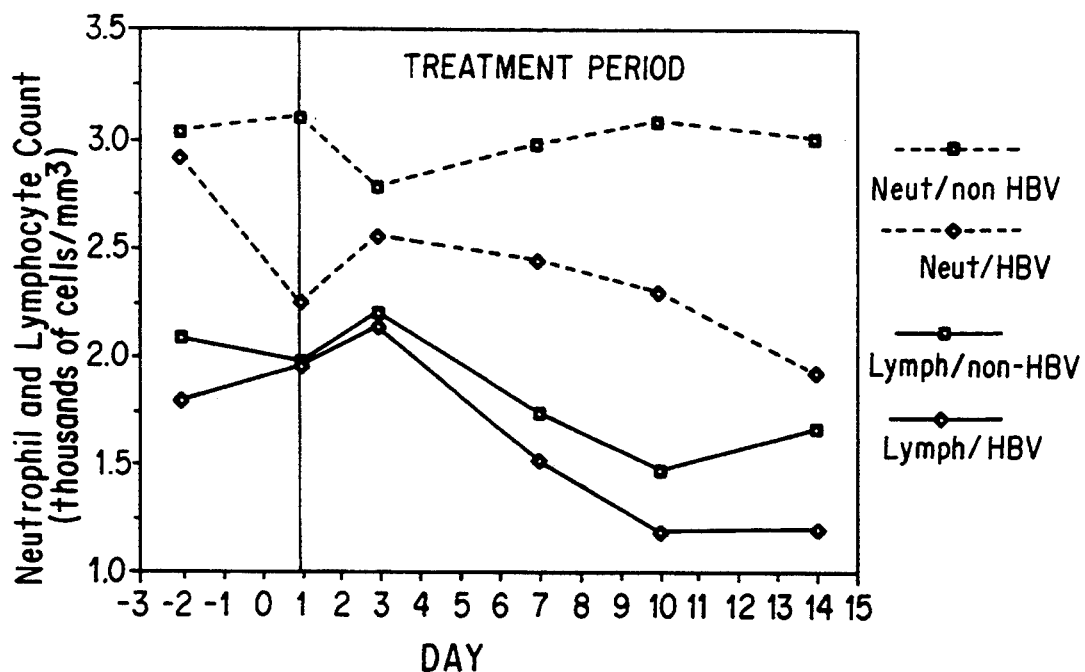
FIG. 13 contrasts the Neutrophil and Lymphocyte Count between the non-hepatitis and hepatitis patients.

FIGS. 12 and 13 contrast the mean WBC, neutrophil and lymphocyte values between the non-hepatitis and hepatitis patients. The increases in liver enzymes during therapy in the hepatitis patients were not significant ($p>0.1$), although two of these patients had substantial spikes in their liver enzymes. Patient 401 had a doubling of his AST and ALT values at the very end of therapy that returned to less than Baseline values by the end of the month of post-treatment follow-up.

Figure 14:
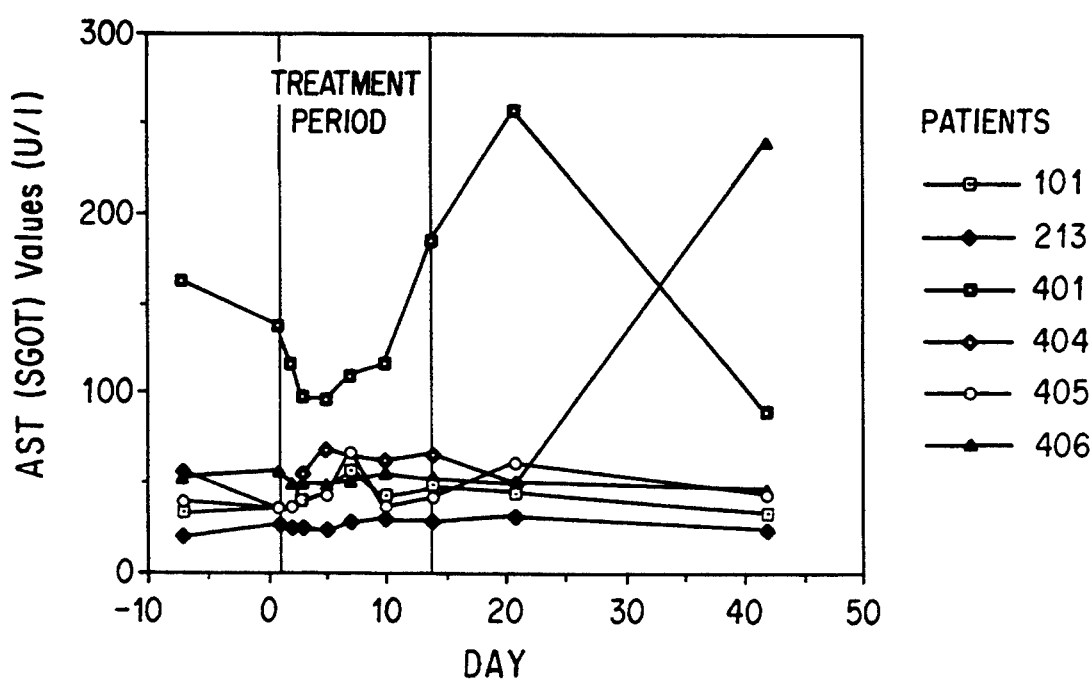
FIG. 14 shows the effect of FIAU on AST of hepatitis patients.
Figure 15:
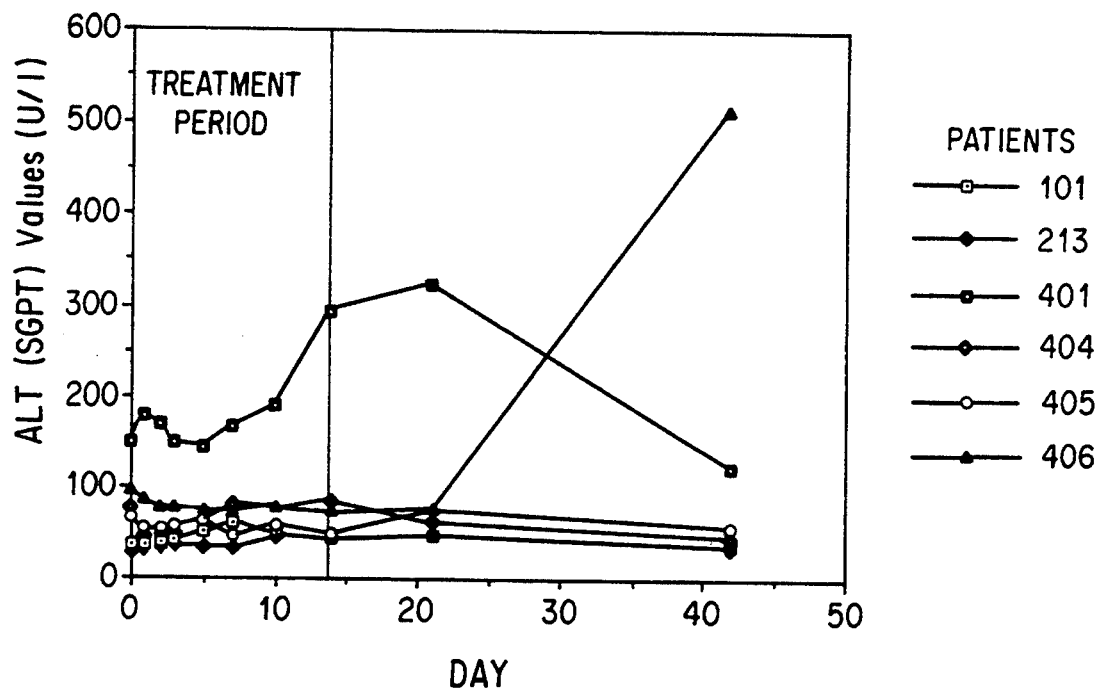
FIG. 15 shows the effect of FIAU on ALT of hepatitis patients.

Patient 406 had an approximate 5-fold increase in his AST and ALT values 28 days after the completion of therapy. These spikes in liver enzymes were unaccompanied by any symptoms, increases in non-laboratory toxicity or clinically important changes in any other laboratory tests, except for a doubling of LDH in Patient 406's serum. The temporal changes in AST and ALT are shown in FIGS. 14 and 15.

Three patients without hepatitis were dosed at 1.7 mg/kg-day. Two (Patients 211 and 212) discontinued after 3 and 4 doses of FIAU, respectively, while the third (Patient 214) discontinued therapy after seven days. All discontinued due to severe fatigue that was accompanied by moderate nausea in all and mild to moderate vomiting in two. Two of the patients were on concurrent anti-emetics. Patient 211 was taking Reglan ® and Patient 214, Compazine ®. It is notable that no biochemical or hematological abnormalities were noted in these patients. As a result of these three consecutive drop-outs, all due to the same symptom, this dose of FIAU was determined to be not tolerated and no additional patients were enrolled into this dose cohort.

The peak and trough values of FIAU and its primary deiodinated metabolite FAU were determined from both the non-hepatitis and hepatitis cohorts dosed at 1.0 mg/kg-day of FIAU. Peak and trough values were very consistent on a per patient basis. Peak and trough values after the initial dose averaged 0.58 and 0.05 µg/ml, respectively, and had reached steady state by Day 3, when these values averaged 1.0 and 0.23 µg/ml. The Day 1 values from Patient 401 were not used in these calculations due to his initial 10× overdose.

The patients were quite similar in the peak and trough plasma levels resulting from dosing at 1.0 mg/kg-day. Table I displays the ranges, means and standard deviations found for peak and trough FIAU values after the initial dose and at steady state.

TABLE I

Observed Ranges, Means and Standard Deviations in Peak and Trough FIAU Concentrations in Plasma

| FIAU (µg/ml) | | Range | | Mean | Std. Dev. |
|---|---|---|---|---|---|
| | | minimum | maximum | | |
| Initial Dose Day 1 | Peak | 0.32 | 0.95 | 0.58 | 0.20 |
| | Trough | 0.00 | 0.13 | 0.05 | 0.04 |
| Steady State | Peak | 0.39 | 1.66 | 0.97 | 0.27 |

TABLE I-continued

Observed Ranges, Means and Standard Deviations in Peak and Trough FIAU Concentrations in Plasma

| FIAU ($\mu$g/ml) | | Range minimum | maximum | Mean | Std. Dev. |
|---|---|---|---|---|---|
| Days 3–14 | Trough | 0.07 | 0.51 | 0.21 | 0.10 |

Figure 16:
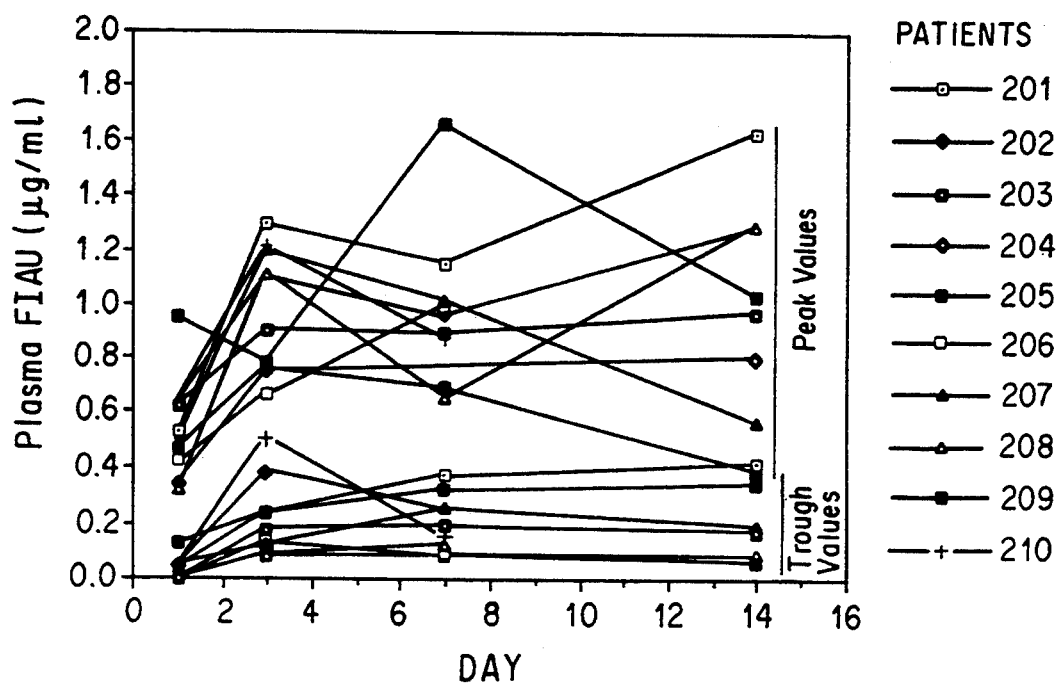
FIG. 16 shows the effect of FIAU on the Plasma levels of FIAU in non-hepatitis patients.
Figure 17:
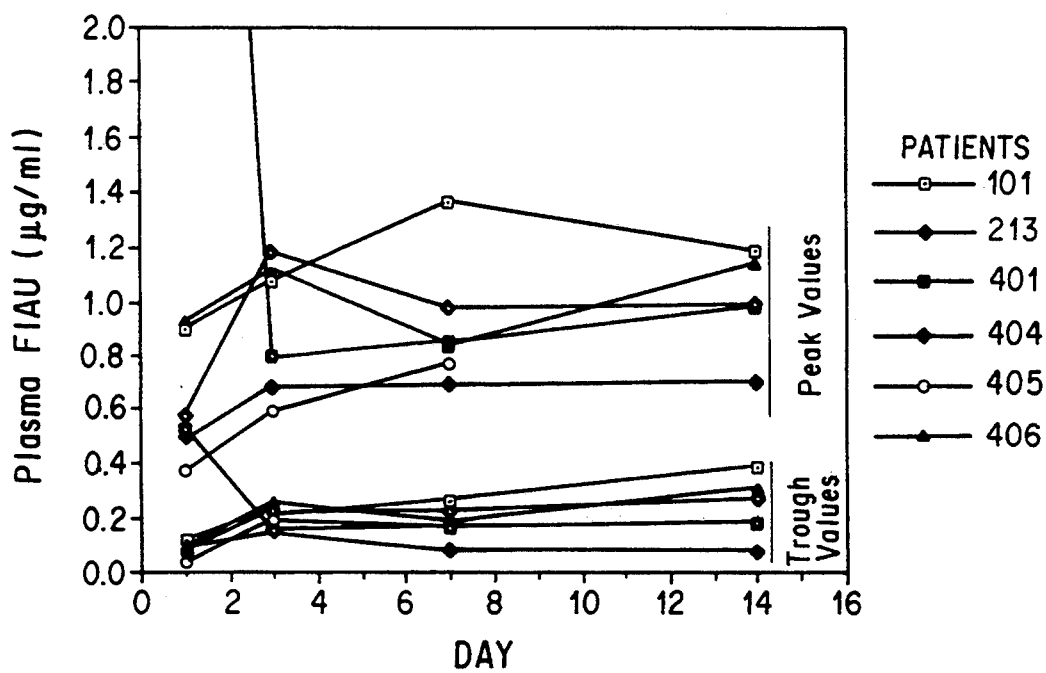
FIG. 17 shows the effect of FIAU on the plasma levels of FIAU on hepatitis patients.
Figure 18:
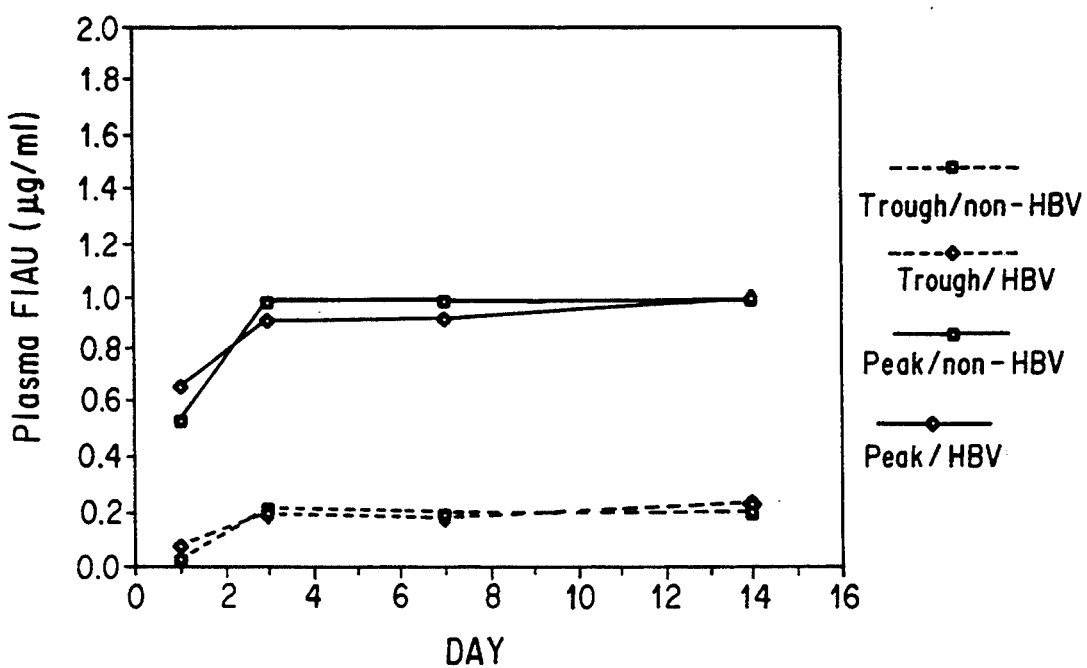
FIG. 18 shows the mean values of the Plasma FIAU in hepatitis and non-hepatitis patients.

There were no appreciable differences in peak or trough values of either FIAU or FAU between the "tolerance" and hepatitis cohorts. FIGS. 16 and 17 show the timeline changes of peak and trough FIAU values for these two populations. Mean values are shown in FIG. 18. FAU levels were uniformly low and rarely exceeded 0.15 g/ml. FAU values were almost always undetectable after the initial dose and increased to very low (average of 0.061 and 0.037 g/ml for peak and trough, respectively) and constant values from Day 3 onward. They showed less variation between peak and trough than the parent compound and did not differ appreciably between the "tolerance" and hepatitis cohorts. There was a trend for the "tolerance" cohort to have had slightly higher FAU values. Neither FIAU nor FAU tended to accumulate in the plasma with continued dosing.

Discussion

FIAU has produced a more profound effect on hepatitis B markers than any drug previously studied and has done so in the HIV-infected population. More than a 70% reduction in HBV DNA was seen in five of the six patients after only two days of dosing. By the end of two weeks, five of six had more than 90% suppression of this marker. During a month of post-treatment follow-up, half of the patients stayed completely or nearly completely suppressed.

In these six patients we have evidence so far that one of the patients whose markers stayed suppressed has seroreverted for the e antigen. Two of the patients had substantial flares in their liver enzymes. One of these had lower liver enzyme values at the end of the month of follow-up than he entered the study with. Follow-up on the second patient is pending. Five of the six patients have shown continuing substantial suppression (>80%) in the amount of HBV DNA polymerase in their serum.

The three patients whose HBV DNA values have rebounded, have rebounded only partially to values between approximately 25 and 50% of baseline. The long term effect of this type of partial rebound is unknown, but does contrast sharply to previous work done with ara-A and ara-AMP. These nucleosides were found to have a rapid and consistent effect on HBV DNA polymerase and HBV DNA similar to FIAU. However, when dosing was stopped, these markers most often very rapidly rebounded to baseline levels and above. Both compounds were found to be too toxic (persistent and severe neuromuscular pain) for the chronic type therapy necessary to maintain suppression of the markers. (Hoofnagle, J. H. et al. *J. Hepatol.* 1986, 3(Suppl. 2):S73–S80; Perrillo, R. et al. *Gastroenterology* 1985, 88:780–786.)

Oral FIAU was relatively well-tolerated by the hepatitis patients for two weeks when dosed TID at 1.0 mg/kg-day. None of these patients discontinued therapy. Nausea, however, in four patients required antiemetic therapy. No serious biochemical abnormalities were noted.

Significant decreases in WBC with an apparent predilection for lymphocytes was seen, especially in the hepatitis patients. The significance of this apparent difference is not clear at this time. The one incident of post-treatment myositis, however, is bothersome and must be kept in mind during further evaluations of this drug. Two of ten non-hepatitis patients did not tolerate 1.0 mg/kg-day and withdrew due to nausea and fatigue. All three non-hepatitis patients dosed at 1.7 mg/kg-day withdrew early also due to fatigue. Therefore 1.0 mg/kg-day is probably close to the maximum dose to be tolerated with TID dosing for two weeks.

It should be remembered that all of the patients in this study are HIV-infected and therefore immune compromised. It is possible that chronic hepatitis B patients without concurrent HIV infection may respond better, perhaps have lower effective doses and tolerate FIAU better.

Summary of Results of Clinical Studies With Immune-Compromised Patients at Daily Submilligram Per Kilogram Dosage of FIAU The results of clinical investigations conducted at submilligram per kilogram daily doses of FIAU are presented below. In this study, the effect of FIAU at 0.5 mg/kg-day on the baseline levels of HBV DNA was evaluated in five HIV-infected patients, four of whom had HBV DNA entry levels under 1000 pg/ml. The fifth patient had an entry baseline serum HBV DNA value above 1000 pg/ml.

Figure 19:
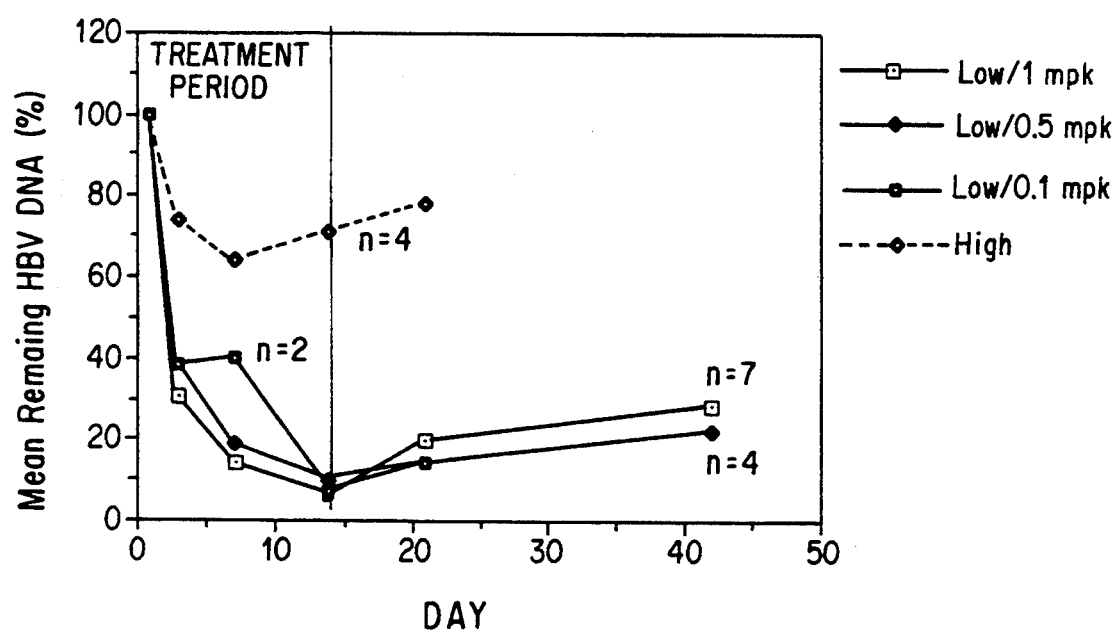
FIG. 19 shows the reduction of HBV marker in patients.

In the four patients with entry HBV DNA levels less than 1000 pg/ml, the average serum concentration of HBV DNA dropped 61% after the first two days of therapy. Average levels were less than 20% of baseline by the end of one week of dosing, and less than 10% by the end of the two week treatment course. Moreover, one month post-treatment average values were still over 75% suppressed. These HBV marker reductions were quite similar to those observed in the patients dosed at 1.0 mg/kg-day (See, FIG. 19). The single patient with a baseline serum HBV DNA value above 1000 pg/ml had an 83% drop in his one week of therapy; thereafter he was dropped from the study due to a hematuria that, most likely, was unrelated to the study.

Five additional patients who did not have HBV DNA present at entry were dosed at 0.5 mg/kg-day. The side effects for the ten patients dosed at 0.5 mg/kg-day were similar to those noted in the patients dosed at 1.0 mg/kg-day. However, some advantageous differences were observed for the lower dose group, such as a lower incidence of mild nausea.

Four patients were dosed at 0.1 mg/kg-day. All had HBV DNA present in their serum at study entry. Two of these patients had serum HBV DNA levels under 1000 pg/ml at the start of dosing. Both responded well, achieving an average 60% reduction at both the Day 3 and One Week visits during therapy and a 93% reduction by the end of therapy at two weeks. A very high level of suppression (86%) was still apparent one week post-treatment. Longer term follow-up is ongoing. These results were again very similar to those obtained for patients dosed at the higher levels of drug.

The two patients with baseline HBV DNA levels over 1000 pg/ml fared less well, with neither patient achieving over a 25% drop in this marker by the end of therapy. It should be noted that in the vast majority of individuals chronically infected with HBV, baseline HBV DNA levels rarely exceed 500–700 pg/ml. However, this baseline HBV DNA level can easily be in excess of 1000 pg/ml in those chronic HBV patients who are concurrently infected with HIV.

Gastrointestinal (G.I.) and neurologic side effects in the four patients dosed at 0.1 mg/kg-day appeared to be remarkably reduced compared to the other two dose groups. In fact, no adverse G.I. effects were seen. In addition, only one incident of fatigue was reported compared to incidences of approximately 40-50% in the other groups. A summary of the adverse effects experienced by some of the patients involved in the various dosage studies conducted are presented in Table II, attached hereto. Where no entry is given, no adverse experience was observed.

Overall, for HIV-infected patients with concurrent chronic hepatitis B, doses of 0.1 to 1.0 mg/kg-day have not produced unacceptable toxicity. Moreover, these dosage range appears to be equally effective in producing a rapid, profound and sustained suppression in serum levels of HBV DNA for patients with baseline values under 1000 pg/ml. At higher levels of serum HBV DNA, no uniformity in the effectiveness of this dosage range was observed. It should be pointed out, however, that in one high baseline patient up to an 83% suppression was observed after one week of therapy. It should also be pointed out that interferon is reported to be effective only in non-HIV infected patients with baseline entry serum HBV DNA levels less than 200 pg/ml.

Additionally, doses of 0.1 mg/kg-day appear to be much better tolerated than either 1.0 or 0.5 mg/kg-day dosage levels. A dosage level of about 0.05 mg/kg-day will elicit even better tolerance in HIV/HBV-infected patients, in general, and in non-HIV/HBV-infected patients, in particular. Moreover, because of the immune suppression found in the HIV-infected population, effective doses in chronic hepatitis patients without concurrent HIV infection are comparable, if not lower, than those found in the present study.

Clinical Studies With Immune-Competent Patients

The adequate tolerance observed at a dosage of 1.0 mg/kg-day, coupled with the antiviral effects presented above, warrant further studies of HBV infection and disease in immuno-competent patients.

To assess the antiviral activity of FIAU against hepatitis B virus, up to 24 patients with chronic hepatitis B will be treated with oral FIAU in doses of 0.05, 0.10, 0.25 or 0.50 mg/kg-day in three divided doses daily for four weeks. Six patients, of which only three can be previous interferon failures, will be initially dosed at 0.10 mg/kg-day. Depending on tolerance and efficacy, the next six patients will be entered at 0.05 or 0.25 mg/kg-day. Sequential dose cohorts, up to the four planned (0.05, 0.10, 0.25 and 0.50) will be studied, until consistent efficacy or lack of tolerance is demonstrated.

Patients will be monitored carefully before, during and after therapy for the effects of FIAU on HBV levels in serum, on serum aminotransferases and other markers of chronic liver disease, and for potential side effects. This is a preliminary dose-finding study which is designed to provide safety and preliminary efficacy data for either a full scale, randomized controlled trial or another dose finding study evaluating longer courses of treatment (two to four months).

Thus, the objective of the present study is to determine a potentially effective and tolerated oral dose of FIAU for treating chronic hepatitis B three times per day for four weeks.

Study Design

This study is an open and uncontrolled evaluation of oral FIAU in the treatment of chronic hepatitis B. Up to four dose cohorts of six patients each will be sequentially studied starting at 0.10 mg/kg-day. Patients will take the medication three times per day for four weeks. Depending on efficacy and tolerance, the next dose cohort will be either 0.05 or 0.25 mg/kg-day. The planned dose cohorts (0.05, 0.10, 0.25 and 0.5 mg/kg-day) will continue to be studied until consistent efficacy or a lack of tolerance has been demonstrated.

Consecutively qualifying patients will be used for each dose group and patients will not be assigned to dose based on either disease severity or expected tolerance. Tolerance will be determined with antiemetic therapy given concomitantly as necessary should a patient experience sustained nausea or two or more episodes of vomiting. Compazine, 10 mg p.o. Q6H or 25 mg p.r. Q12H will be used.

Patients

As many as 24 patients with chronic hepatitis B will be treated.

Inclusion Criteria a. Age 18 to 70 years, male or female.
b. Presence of hepatitis B surface antigen (HBsAg) present in serum for at least six months.
c. Presence of HBeAg and HBV DNA in serum, documented on three or more occasions at least one month apart, during the six months before entry into the trial (for example, at two months before entry, one month before entry and at entry).
d. Presence of elevated serum alanine aminotransferase (ALT) activity, such that the average levels are $>50$ U/L on three or more determinations taken at least one month apart during the six months before entry.
e. Compensated liver disease as shown by prothrombin time less than three seconds prolonged, serum albumin greater than 3.0 gm %, serum bilirubin less than 4.0 mg % and no history of ascites, wasting, hepatic encephalopathy or bleeding esophageal varices.

Exclusion Criteria a. Serologic positivity for anti-HIV, antibody to hepatitis-C virus (anti-HCV) or to hepatitis delta virus (anti-HDV).
b. Pregnancy or, in patients capable of bearing or fathering children, inability to practice adequate contraception.
c. Significant systemic illness other than liver disease, including congestive heart failure, renal failure, uncontrolled diabetes mellitus such that more than one major medication is needed on a regular basis to control symptoms or biochemical features of disease.
d. Pre-existing bone marrow compromise: hematocrit $<30\%$, white blood cell count $<2500$ mm$^3$ platelets $<50,000$ mm$^3$.
e. Antiviral or immunologic therapy within the last six months.
f. Patients who have never received a course of interferon and who have severe disease as shown by cirrhosis on liver biopsy or an aspartate aminotransferase level of greater than 100 U/L (average of three determinations before evaluation) will be advised to receive a course of alpha interferon.

Treatment

Patients who meet the eligibility criteria will start on therapy, generally as outpatients one to two weeks after the in-hospital evaluation. Up to four doses will be sequentially evaluated. The initial six patients will receive 0.10 mg/kg-day for four weeks. If this dose is found to inhibit HBV DNA significantly (>50% by four weeks), six patients will be treated with 0.05 mg/kg-day.

If tolerance is adequate at 0.10 mg/kg-day, six patients will receive 0.25 mg/kg-day for four weeks. The final six patients will receive 0.50 mg/kg-day for four weeks if needed for better efficacy and if tolerance has been adequate at the lower doses.

The FIAU will be administered by mouth in three equally divided doses daily. FIAU is provided as a 1 mg/ml syrup. Patients will be instructed on how to measure and self-administer the FIAU solution using oral dosing syringes. Dosing compliance will be monitored by measuring the residual FIAU solution returned at the weekly outpatient visit.

This study will not be blinded or randomized. It is prudent to start with a low dose because of the paucity of information on the safety of FIAU when given for four weeks. Some patients entering this protocol will have received interferon in the past without a lasting response. For this reason, no more than three patients who have previously failed on interferon therapy will be entered at each FIAU dose level.

The sequential dose cohort approach, starting at an intermediate dose will avoid treating too many patients at a dose of FIAU that is clearly ineffective. Starting at an intermediate dose will also allow avoidance of excessive toxicity. This approach will mandate that all patients be entered into a dose cohort and wait for the preliminary efficacy results and safety results before starting a second dose group.

The side effects that will be monitored will include gastrointestinal irritation, bone marrow suppression, neurologic, and muscular toxicity.

Efficacy Assessment

Activity of FIAU against hepatitis B virus will be assessed by monitoring levels of HBV DNA. An inhibition of HBV DNA activity of at least about 50% by the fourth week of treatment will be considered significant antiviral activity. The dose levels of FIAU will be compared based upon the degree of inhibition of serum levels of HBV DNA.

In addition, FIAU will be evaluated for its potential long-term effects on chronic HBV infection. Long-term response will be assessed based upon clearance of HBV DNA and HBeAg from the serum within six months of starting treatment followed by a fall of serum aminotransferase activities to within the normal range or to within 1.5 times the upper limit of the normal range within one year of starting therapy. These criteria are typical of those used to assess antiviral agents in chronic hepatitis B.

Remission or "response" occurs spontaneously in 5–10% of patients with chronic hepatitis B followed for one year. Although the size of this pilot study is not adequate to assess whether FIAU increases remissions in this disease above what would be expected by chance, this study will provide an estimate of the response rate to FIAU (if any) which would be useful in designing a controlled trial to assess long-term efficacy of treatment. This assessment was made, and the efficacy results are discussed below.

Efficacy Results

Oral administration of FIAU in normal patients, i.e., non-immune-comprimised, at various low dosage levels indicates that FIAU is effective at reducing dramatically, serum levels of HBV markers, namely, HBV DNA and HBV DNA polymerase. A detailed summary of the efficacy results for the reduction of HBV DNA polymerase and HBV DNA levels is presented in Tables III and IV, respectively. It can be seen from these Tables that striking reductions are achieved over a 4-week treatment period, which reductions persist at such substantially reduced levels over the post-treatment period examined for the majority of the patients.

TABLE III

Summary Of Effect Of Oral FIAU On Plasma HBV DNA Polymerase Levels of Immune-Competent Patients At 0.1, and 0.25, and 0.05 mpk Dosage Levels

| Patient | Prior IFN | HBV DNA Polymerase (cpm) | | | | | | |
|---------|-----------|-------|-------|-------|--------|--------|--------|--------|
|         |           | Day 1 | Day 3 | Day 8 | Week 2 | Week 3 | Week 4 | Week 5 |
| 1A[a]   | yes       | 1208   | 348   | 119   | 90     | 144    | 93     | 84     |
| 2A[b]   | no        | 3340   | 721   | 550   | 507    | 360    | 205    | 368    |
| 3A[c]   | yes       | 3,000  | 1,550 | 843   | 977    | 303    | 310    | 657    |
| 4A      | no        | 1,500  | 440   | 164   | 118    | 69     | 74     | 169    |
| 5A      | no        | 1,174  | 251   | 145   | 136    | 86     | 99     | 127    |
| 6A[d]   | no        | 3,000  | 610   | 169   | 142    | 148    | 165    | 324    |
| 1B      | no        | 43,752 | 7,841 | 5,129 | 3,395  | 2,012  | 834    |        |
| 2B      | yes       | 835    | 182   | 81    | 129    | 63     | 42     |        |
| 3B      | no        | 10,833 | 2,115 | 1,481 | 2,752  | 1,602  | 1,076  |        |
| 4B[e]   | yes       | 2,752  | 1,302 | 213   | 105    |        |        |        |
| 5B[f]   | no        | 2,454  | 506   | 131   | 45     |        |        |        |
| 6B[g]   | no        | 7,422  | 1,482 | 772   | 260    |        |        |        |
| 1C[h]   | no        | 1,318  | 748   | 348   |        |        |        |        |

TABLE III-continued

Summary Of Effect Of Oral FIAU On Plasma
HBV DNA Polymerase Levels of Immune-Competent
Patients At 0.1, and 0.25, and 0.05 mpk Dosage Levels

| Patient | Prior IFN | HBV DNA Polymerase (cpm) | | | | | | |
|---|---|---|---|---|---|---|---|---|
| | | Day 1 | Day 3 | Day 8 | Week 2 | Week 3 | Week 4 | Week 5 |
| 2C | yes | 3,365 | 1,509 | 908 | | | | |

A = 0.1 mpk Dose
B = 0.25 mpk Dose
C = 0.05 mpk Dose
? = Patient had received interferon treatment previously without success
a = Experienced mild fatigue on Days 8 and 28.
b = Experienced mild fatigue on Days 3, 8, 14, 21, 28, and Week 5.
c = Experienced mild fatigue on Days 14 and 21.
d = Experienced mild nausea on Days 3, 7, 14, and 21 and mild fatigue on Days 7, 14, and 18.
e = Experienced mild fatigue on Days 14, 21, 28, Week 5, and Month 2.
f = Experienced mild nausea on Day 3.
g = Experienced mild fatigue on Days 14, 21, 28, Week 5, and Month 2.
h = Experienced mild fatigue on Day 8.

TABLE IV

Summary Of Effect Of Oral FIAU On Plasma
HBV DNA Levels of Immune-Competent At mpk Dosage Levels

| Patient | IFN? | HBV DNA (pg/ml) | | | | | | | | |
|---|---|---|---|---|---|---|---|---|---|---|
| | | Day 1 | Day 3 | Day 8 | Week 2 | Week 3 | Week 4 | Week 5 | Month 1 | Month 2 |
| 1A | yes | 68.1 | 23.2 | 16.8 | 9.3 | 6.4 | 0.0 | 4.1 | 4.3 | 13.8 |
| 2A | no | 306.2 | 110.6 | 100.1 | 94.5 | 42.2 | 31.4 | 42.4 | 4.8 | 11.7 |
| 3A | yes | 307.7 | 208.7 | 178.8 | 223.2 | 122.1 | 78.3 | 76.1 | 34.2 | 58.4 |
| 4A | no | 18.1 | 12.3 | 8.8 | 7.3 | 3.2 | 2.5 | 8.7 | 4.4 | 5.9 |
| 5A | no | 71.3 | 27.8 | 9.7 | 17.9 | 9.0 | 7.4 | 21.9 | 18.6 | 26.1 |
| 6A | no | 172.6 | 75.6 | 27.6 | 25.2 | 22.8 | 21.8 | 67.9 | 138.5 | 172.9 |
| 1B | no | 975.8 | 742.7 | 718.9 | 492.9 | 373.2 | 237.9 | 376.3 | 4.9 | |
| 2B | yes | 63.9 | 23 | 17.5 | 8.0 | 10.6 | 7.2 | 24.1 | 23.4 | |
| 3B | no | 799.1 | 472.3 | 204.2 | 182.6 | 68.3 | 69.6 | 6.4 | 100.6 | |
| 4B | yes | 196.3 | 103.5 | 47.1 | 32.4 | 31.1 | 34.0 | 89.9 | 242.5 | |
| 5B | no | 110.3 | 40.4 | 15.9 | 9.3 | 8.3 | 7.9 | 6.8 | 2.7 | |
| 6B | no | 141.1 | 79.9 | 60.7 | 26.6 | 44.2 | 41.7 | 96.3 | 116.6 | |

A = 0.1 mpk Dose
B = 0.25 mpk Dose

Figure 20:
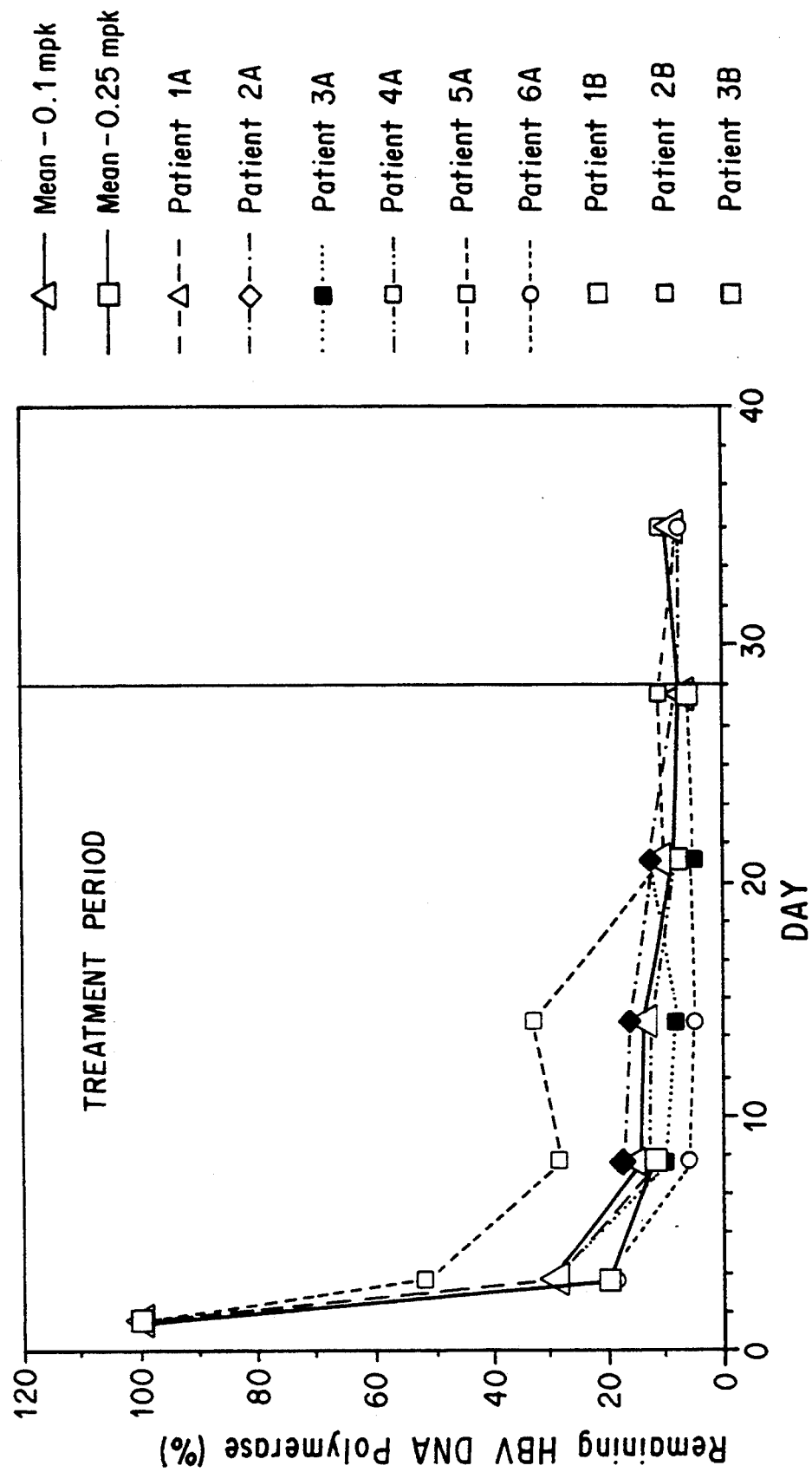
FIG. 20 shows effects of FIAU on plasma HBV DNA Polymerase Levels in patients.

In FIG. 20, one observes that up to an 80–90% reduction of the initial HBV DNA polymerase level is achieved within the first few days. These low levels persist even after treatment has ended.

Table V presents the mean percent change in the HBV DNA serum levels at Week 4 of FIAU oral treatment. At a dosage cohort of 0.05 mpk (mg/kg-day), a mean reduction of 30 percent from initial levels is achieved. At slightly higher dosage cohorts, 0.1 and 0.25 mpk, the mean percent reduction is 88 and 84 percent, respectively. Interestingly, 2 of 6 patients in the 0.25 mpk dosage cohort "sero-converted", i.e., failed to exhibit the presence of hepatitis B surface antigen.

TABLE V

DOSAGE GROUP SUMMARY
Immuno-Competent Patients

| Dose (mpk) | 0.05 | 0.1 | 0.25 |
|---|---|---|---|
| Number with 1 month follow-up | 6 | 6 | 6 |
| Mean % change of HBV DNA at Week 4 of FIAU | (n = 4) −31% | (n = 6) −88% | (n = 6) −84% |
| Number HBeAg-negative at latest follow-up | 0 | 0 | 2 |

Figure 21:
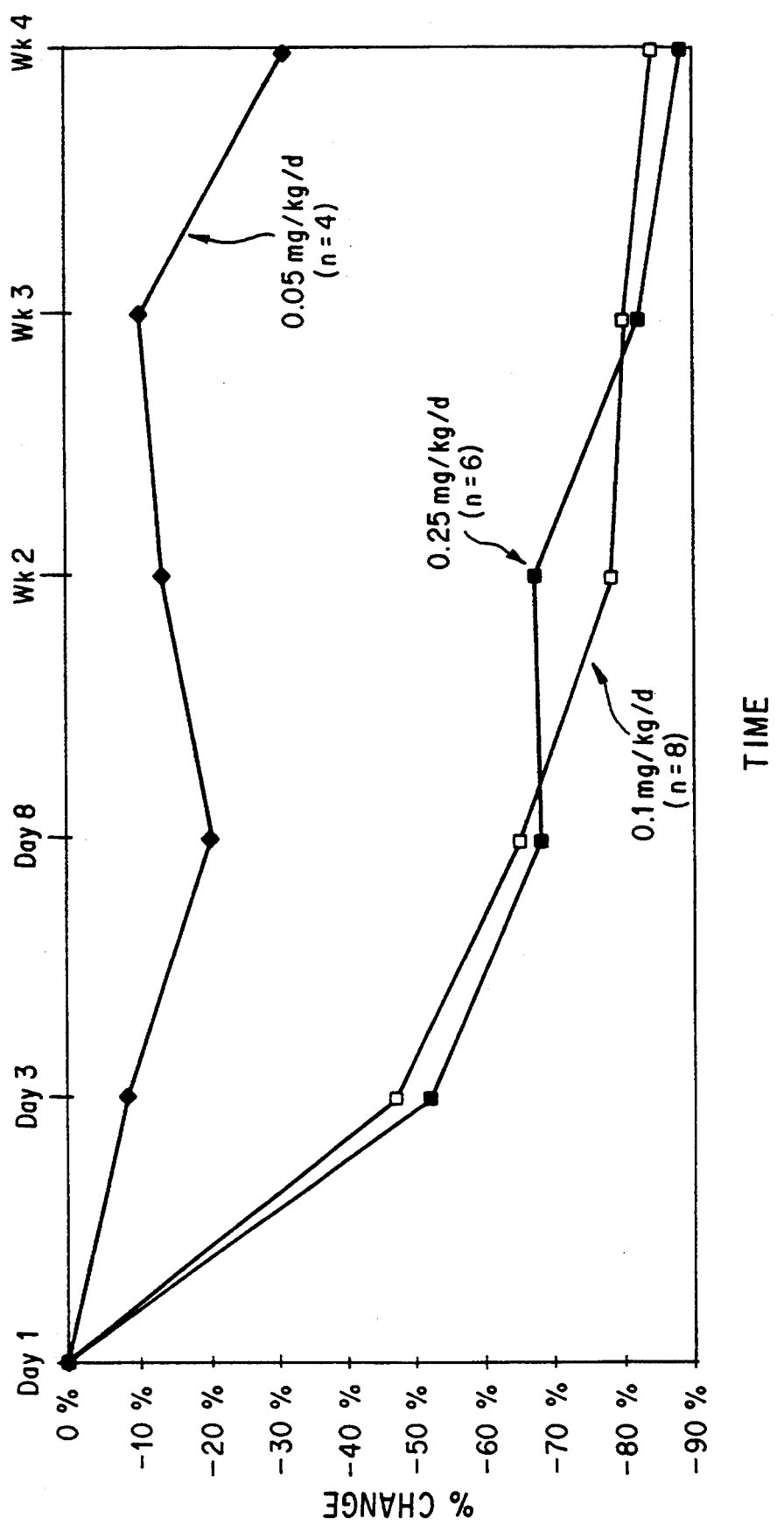
FIG. 21 shows the mean percentage change in HBV DNA by dose.
Figure 22:
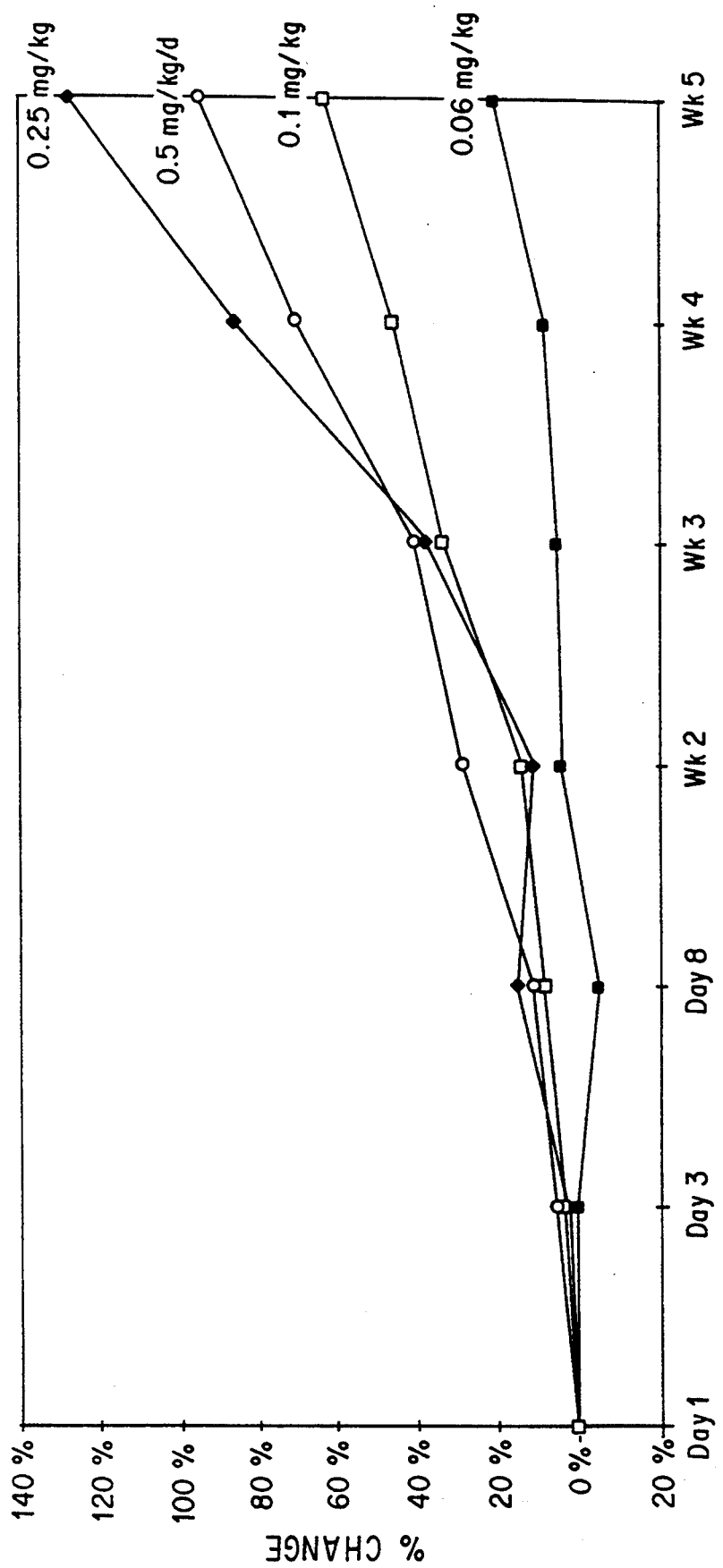
FIG. 22 shows the mean percentage change of ALT by dose.
Figure 23:
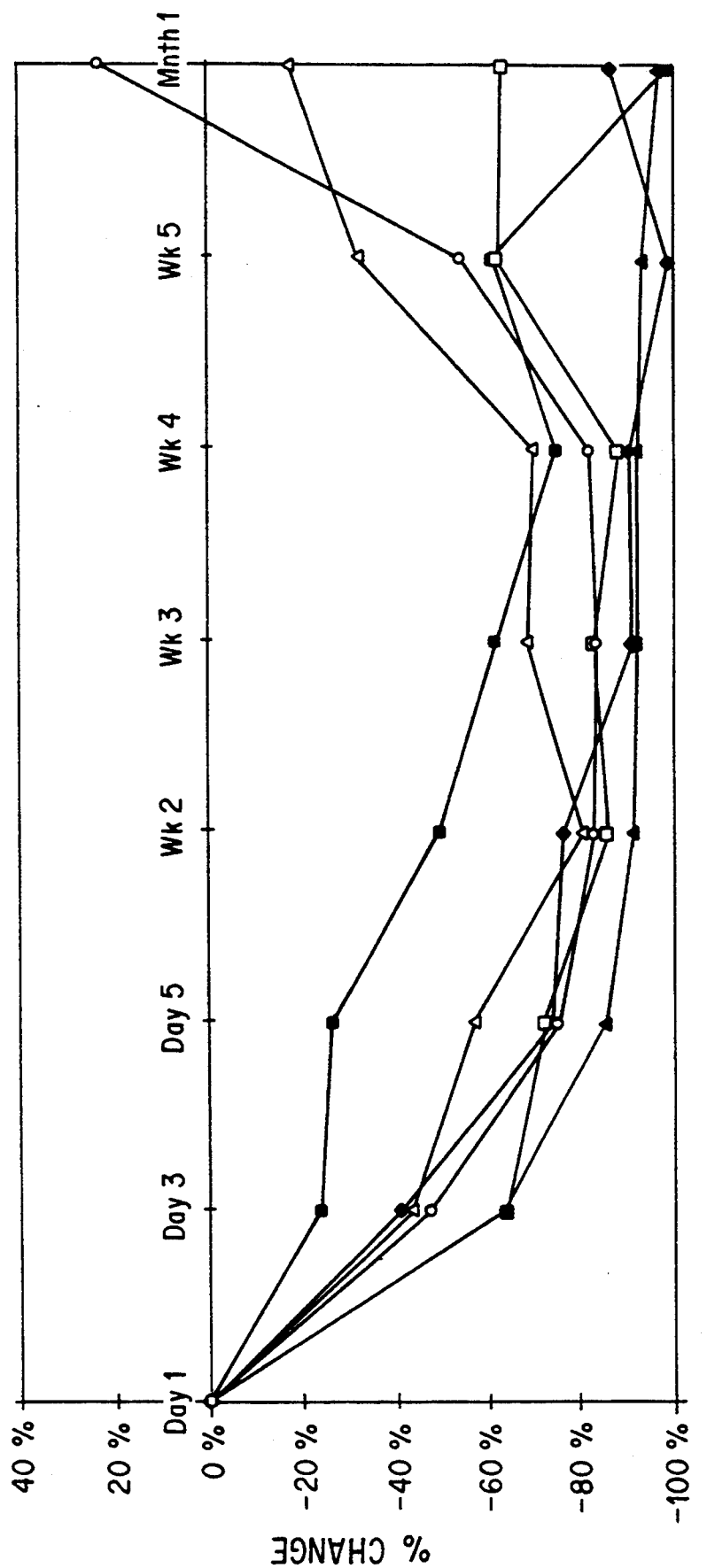
FIG. 23 shows the percentage change of HBV DNA.
Figure 24:
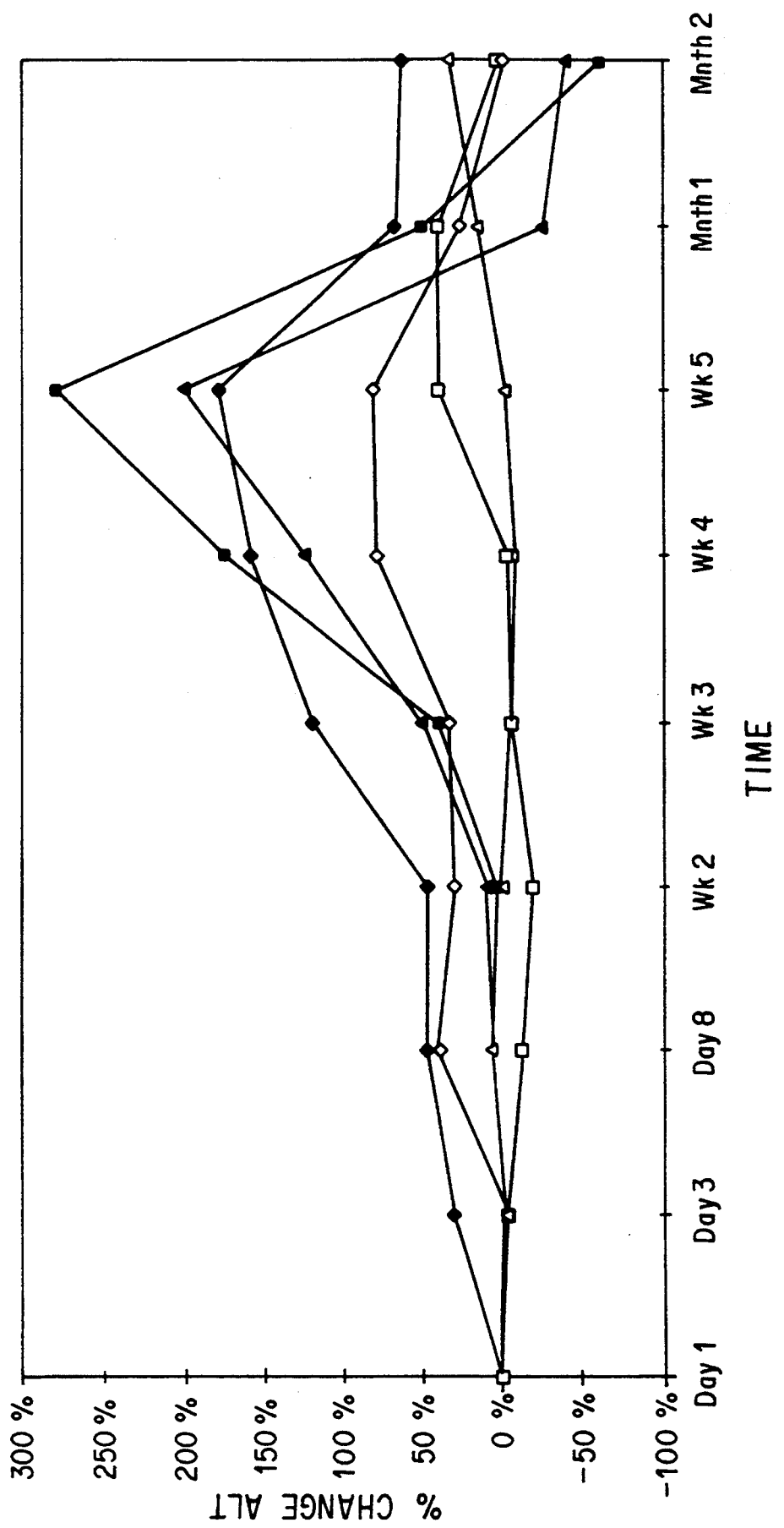
FIG. 24 shows the percentage change of ALT.
Figure 25:
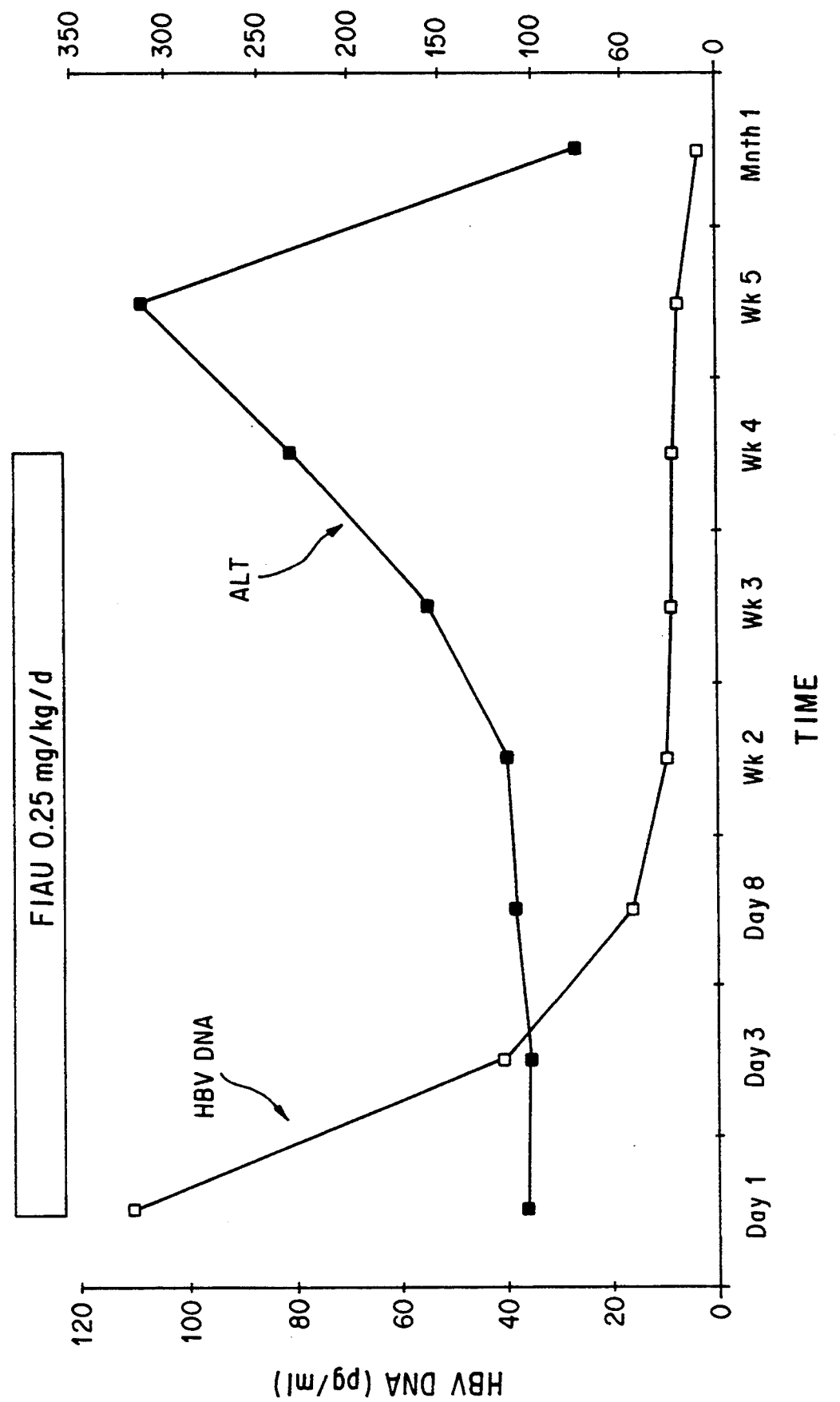
FIG. 25 shows changes in HBV DNA and ALT of a patient to a specific dose of FIAU.

The mean percentage change in HBV DNA by dose is presented graphically in FIG. 21. The mean percentage change of ALT by dose is presented graphically in FIG. 22. Likewise, graphical presentations of the results of 0.25 mpk Dose levels by patient may be found in FIG. 23 (percentage change of HBV DNA), and FIG. 24 (percentage change of ALT). FIG. 25 illustrates the response of patient 5B to 0.25 mpk oral FIAU.

EXAMPLES OF ANTIVIRAL COMPOSITIONS

FIAU Syrup

An FIAU syrup formulation suitable for use as a pharmaceutical antiviral composition is described below. In particular, the syrup formulation is prepared by combining the components listed, with the amounts representative of the content of the listed component, respectively, in 1 ml of syrup.

| FIAU | 10 mg |
|---|---|
| Glycerin, USP | 0.10 ml |
| Alcohol, USP | 0.10 ml |
| Propylene Glycol, USP | 0.10 ml |
| Purified Water, USP | 0.10 ml |
| FD&C Red #40 | 0.025 mg |
| FD&C Yellow #5 | 0.010 mg |
| FD&C Blue #1 | 0.001 mg |
| Artificial Flavors | 0.001 ml |
| Maltitol syrup qs ad | 1.0 ml |

To a suitable vessel equipped with agitation and a heat source, add the glycerin, alcohol and propylene glycol. Mix for approximately five minutes to obtain a clear, homogeneous solution, while heating to approximately 40° C. Next add the FIAU (or FIAC, as the case might be), maintaining agitation and rinsing well with the purified water. Mixing is continued for at least twenty minutes or until a clear, complete solution is obtained. Next, add the coloring and flavoring agents, while maintaining agitation for five minutes. Let the mixture cool to room temperature, if necessary, and bring the mixture to the final volume with the maltitol syrup. Mix gently to avoid incorporation of air bubbles for an additional 30 minutes. The batch may be tightly covered and held for final filtration and packaging. Filter the syrup through a 1.0 micron membrane filter or equivalent and package in final containers.

The amount of the active ingredient can be adjusted so that variable amounts of antiviral agent can be administered per ml of syrup (e.g., 0.25, 0.5, or 5 mg of FIAU).

Other examples of syrups, particularly flavored ones, are present below.

| FIAU 10 mg/ml - Chocolate Flavor | |
| --- | --- |
| FIAU | 10 mg |
| Purified Water, USP | 0.10 ml |
| Glycerin, USP | 0.10 ml |
| Alcohol, USP | 0.10 ml |
| Propylene Glycol, USP | 0.10 ml |
| FD&C Red #40 | 0.025 mg |
| FD&C Yellow #5 | 0.10 mg |
| FD&C Blue #1 | 0.001 mg |
| Artificial Gran Manier | 0.0005 ml |
| Artificial Chocolate | 0.0005 ml |
| Syrup NF qs ad | 1.0 ml |

Excipient Rationale:

Vehicle: Maltitol syrup, water, glycerin, alcohol and propylene glycol: possible substitutions include glucose, dextrose, mannitol, saccharin, sucrose, sorbitol, honey, mucilages, and other flavored syrups.

Flavors: Orange/vanilla, chocolate/gran marnier, and cherry: possible substitutions include raspberry, lemon, spearmint, or citric. This product can also contain no flavor.

Colors: FD & C Red #40, FD & C Blue #1 and FD & C Yellow #5. Other colors can be substituted or the product can be without colors.

Note: This product can contain preservatives or suitable buffering system.

| FIAC 10 mg/ml - Cherry/Orange Flavor | |
| --- | --- |
| FIAU | 10 mg |
| Purified Water, USP | 0.10 ml |
| Glycerin, USP | 0.10 ml |
| Alcohol, USP | 0.10 ml |
| Propylene Glycol, USP | 0.10 ml |
| FD&C Red #40 | 0.05 mg |
| FD&C Yellow #5 | 0.010 mg |
| Natural Orange Flavor | 0.0075 ml |
| Artificial Vanilla | 0.0035 ml |
| Maltitol Syrup qs ad | 1.0 ml |

Excipient Rationale:

Vehicle: Maltitol syrup, water, glycerin, alcohol and propylene glycol: possible substitutions include glucose, dextrose, mannitol, saccharin, sucrose, sorbitol, honey, mucilages, and other flavored syrups.

Flavors: Orange/vanilla, chocolate/gran marnier, and cherry: possible substitutions include raspberry, lemon, spearmint, or citric. This product can also contain no flavor.

Colors: FD & C Red #40, FD & C Yellow #5. Other colors can be substituted or the product can be without colors.

Note: This product can contain preservatives or suitable buffering system.

Oral Solution

For initial investigation, FIAC will be administered as an oral solution, prepared prior to use. Solutions will be prepared by dissolving the FIAC Powder for Oral Solution (containing neat FIAC active ingredient) with purified water prior to administration.

Component: FIAC, 1-(2'-deoxy-2'-fluoro-$\beta$-D-arabinofuranosyl)-5-iodocytosine (neat)

Composition: FIAC will be provided in specified pre-weighed amounts (e.g., from about 0.05 to about 500 mg).

Packaging: Individually weighed doses of FIAC will be packaged in 4 oz. amber glass ovals (i.e., Owens-Illinois P-804)

Closure: Owens-Illinois Clic Lock ®

Method of Preparation

The FIAC oral solution is prepared by the following procedure:

To each dosage unit of FIAC powder for solution:

a. Add 100 ml of purified water USP
b. Disperse with the aid of an ultrasonic bath (10 minutes) or by intermittent shaking (~30 minutes)
c. Observe individual bottles visually to assure complete solution prior to use
d. Maintain unused portion of prepared solution under refrigeration
e. Note: If refrigerated—carefully observe for complete solution and gently warm to room temperature with agitation (ultrasonic bath may be used if available) to redissolve if crystals are present
f. Discard any unused solution after one week from preparation FIAC Powder for Oral Solution: General Methods of Manufacture and Distribution Clean bottle by blowing with filtered compressed air (filter 0.45 u). Individually weigh and record FIAC for each dose on an analytical balance (i.e. Sertorius or equivalent). Afterward, transfer weighed dose of FIAC to clean bottle and check weight for complete transfer using individual bottle tare on a suitable balance (i.e. Mettler top load model) or equivalent. Finally, cap individual bottles after checking weight and hold for release and labeling.

The specifications for FIAC Powder for Oral Solution are treated as a unit dose due to the nature of the product. It is recognized that the resulting solution product is a multiple dose experimental dosage form.

The methods of testing are drawn directly from the assay procedure for active substance since the experimental unit contains only neat active substance.

| Specifications | Limits |
| --- | --- |
| Appearance | Crystalline powder, white to off-white |
| Identification, HPLC | Conforms with standard |
| Solution Description | Clear, colorless solution |
| Assay for FIAC and Related Substances | |
| FIAC | 95.0–105.0% of label claim |
| FIAU | 2.0% maximum |
| Other Related Substances | 2.0% maximum |

One, Five and Ten Milligram Capsules

Lower dosage range capsules were prepared as follows. Due to content uniformity considerations, a new technique referred to as Moisture Activated Dry Granulation, (MADG), was used to prepare the capsule blends. This technique is briefly described below:

MADG combines the ease of manufacture of a direct blend formulation with the advantages of a wet granulation. A modified version of the agglomeration step in wet granulation is utilized, however, no drying step is required. Briefly, this granulation technique involves blending the drug with an excipient ("carrier"—e.g. lactose) and a dry binder (e.g., PVP). This blend is then moistened using a small amount of water (1–3% of the formula weight). This moisture activates the dry binder and makes the drug adhere to the carrier particles. Moisture distributing agents (e.g. microcrystalline cellulose) and additional excipients are then added and the granulation process is complete. The resultant granulation provides good content uniformity as well as a free flowing blend for encapsulation or tabletting.

The choice and levels of excipients for the low dosage capsules can be determined as needed by one skilled in the art. Also, the FIAU bulk can be passed through a 200 mesh screen rather than a 100 mesh screen for content uniformity considerations.

FIAU Sodium Salt

FIAU sodium salt for injection is a lyophilized sodium salt of FIAU. The sodium salt is prepared by allowing FIAU to react with sodium hydroxide in situ during preparation of the solution for lyophilization. The lyophilized cake is white in color.

A clinical lot of FIAU sodium salt for injection was reconstituted for stability studies with Sterile Water for Injection, USP, 0.9% Sodium Chloride Injection, USP, and 5% Dextrose Injection, USP. The solutions were stored at room temperature (25° C.). Chemical potency, impurities and degradation products were monitored by HPLC. The solution pH and physical appearance were also monitored. The chemical potency data were statistically analyzed.

These studies support a utility time of 48 hours storage at room temperature (25° C.) for the following diluents and concentrations, provided that the preconstituted vials have been stored at room temperature (25° C.) and have not aged beyond their expiration date. Each vial reconstituted with 2.2 ml of Sterile Water for Injection, USP, yielding a solution concentration of 50 mg/ml. Lower concentrations can be prepared with the appropriate adjustments of the respective components.

Alternatively, the above solution when further diluted with Sterile Water for Injection, USP, 0.9% Sodium Chloride Injection, USP or 5% Dextrose Injection, USP, yielding a solution concentration of 0.2–5 mg/ml.

| 8.5. FIAU Capsule (1–10 mg) | | | |
|---|---|---|---|
| Typical Components | | | |
| FIAU | 3.03% | 10.00 | 1–10 |
| Microcrystalline Cellulose (Avicel ®) | 20.0% | 66.00 | 59–73 |
| Magnesium Sterate, USP | 0.5% | 1.65 | 1.5–1.8 |
| Explotab ® | 2.0% | 6.60 | 5.9–7.3 |
| Lactose, Hydrous USP qs ad | —76.03 | 250.80 | 225–275 |
| Fill Weight | | 330 mg | |

-continued

| 8.5. FIAU Capsule (1–10 mg) | |
|---|---|
| Typical Components | |
| Capsule Size | #1 |

Excipient Rationale
 a. Diluent—microcrystalline cellulose (Avicel ®), lactose, hydrous. Possible substitutions: Lactose, anhydrous.
 b. Lubricant—magnesium sterate; possible substitutions: Talc, calcium sterate, stearic acid, magnesium salts.
 c. Disintegrant—Explotab ®; possible substitutions: Starch, povidone XL, sodium starch glycolate, croscarmelose, methylcellulose, carboxymethyl cellulose.

Method of Manufacture
 a. Mix FIAU with an equal portion of lactose.
 b. Gradually add remainder of lactose and mix well.
 c. Combine Avicel ®, Explotab ® and magnesium sterate and mix well.
 d. Combine the FIAU/lactose mixture (Step 2) with the Avicel ® mixture (Step 3) and mix until sufficiently blended (~10 min. minimum).

| 8.6. FIAU Tablets (1–10 mg): Wet Granulation/ Direct Compression Method | | | | |
|---|---|---|---|---|
| Typical Components | % | % Range | FIAU Tablet, 5 mg. mg/cap | FIAU Tablet, 10 mg. mg/cap |
| FIAU (5%) | a | 0.25–5 | 5 | 10 |
| Lactose (55%) | a | 40–70 | — | — |
| PVP (15% in water) | a | 10–20 | 60.5 | 60.5 |
| Avicel PH101 | 56.5% | 40–75 | 565 | 565 |
| Lactose | 31.0% | 20–50 | 310 | 310 |
| Explotab ® | 5.0% | 2–10 | 50 | 50 |
| Sterotex K | 1.0% | 0.5–5 | 10 | 10 |
| Magnesium Sterate, USP | 0.5% | 0.2–2 | 5 | 5 |
| Net Tablet Weight | | | 200 mg | 400 mg | a = The combined percentage of the first three items is 6%.

Excipient Rationale
 a. Diluent—lactose, hydrous. Possible substitutions: Lactose, anhydrous, microcrystalline cellulose (Avicel ®).
 b. Lubricant—magnesium stearate; possible substitutions: Talc, calcium stearate, stearic acid, magnesium salts.
 c. Disintegrant—possible substitutions: Starch, povidone XL, sodium starch glycolate, methylcellulose, carboxymethyl cellulose.
 d. Binder—Sterotex K, possible substitutions: starch, gelatin, sugars (sucrose, glucose, etc.), carboxymethylcellulose, methylcellulose, polyvinyl pyrrolidone.

Method of Manufacture
 a. Mix the FIAU and lactose together, wet the mixture with the 15% Solution on PVP in water.
 b. Dry the granulation overnight at 40 degrees C.
 c. Pass the dried granulation through a 10 mesh screen and then through a 20 mesh screen.
 d. Mix the magnesium stearate and sterotex K together and then add the explotab.
 e. Combine the two mixture obtained in Step c and d above.
 f. Add the Avicel, lactose and mixture obtained in Step e to the dry blender.
 g. Allow the mixture to blend for 15 minutes.

h. Compress the tablet to the specified weight.

| Description | 1 mg Tablet | 2 mg Tablet |
| --- | --- | --- |
| Diameter | 9 mm | 9 mm |
| Thickness | 4.0 ± 0.5 mm | 6.0 ± 0.5 mm |
| Hardness | 3–10 kg | 3–10 kg |

FIAU Tablets (1–10 mg).

Direct Compression Method

| Typical Components | % | % Range | FIAU Tablet, 5 mg. mg/cap | FIAU Tablet, 10 mg. mg/cap |
| --- | --- | --- | --- | --- |
| FIAU (100 mesh) | 2.5% | 0.2–2.5 | 5 | 10 |
| FIAU (100 mesh) | 2.5% | 0.2–2.5 | 5 | 10 |
| Avicel PH101 | 55.0% | 40–75 | 110 | 220 |
| Lactose, Hydrous USP | 36.% | 25–55 | 72 | 144 |
| Explotab ® | 5.0% | 2–10 | 10 | 20 |
| Sterotex K | 1.0% | 0.5–5 | 2 | 4 |
| Magnesium Sterate, USP | 0.5% | 0.2–2 | 1 | 2 |
| Net Table Weight | | | 200 mg | 400 mg |

Excipient Rationale a. Diluent—microcrystalline cellulose (Avicel®), lactose, hydrous. Possible substitutions: Lactose, anhydrous.

b. Lubricant—magnesium stearate; possible substitutions: Talc, calcium stearate, stearic acid, magnesium salts.

c. Disintegrant—Explotab ®; possible substitutions: Starch, povidone XL, sodium starch glycolate, croscarmelose, methylcellulose, carboxymethyl cellulose.

d. Binder—Sterotex K, possible substitutions: starch, gelatin, sugars (sucrose, glucose, etc.), carboxymethylcellulose, methylcellulose, polyvinyl pyrrolidone.

Method of Manufacture a. Mix the magnesium stearate and Sterotex K in a plastic bag.

b. Add the Explotab ® to the mixture obtained in Step b.

c. Add the FIAU to the mixture obtained in Step b.

d. Add the Avicel PH101, lactose and the mixture obtained in Step c in layers in the twin shell dry blender.

e. Mix for 15 minutes.

f. Compress the tablet at the specified weight.

| Description | 1 mg Tablet | 2 mg Tablet |
| --- | --- | --- |
| Diameter | 9 mm | 9 mm |
| Thickness | 3.5 ± 0.5 mm | 7.0 ± 0.5 mm |
| Hardness | 3–10 kg | 3–10 kg |

Water Soluble FIAC Ointment (1–100.0 mg/g)

| Typical Component | FIAC Ointment, 5% mg/g | % | % Range |
| --- | --- | --- | --- |
| FIAC | 50.0 | 5.0 | 0.1–10.0 |
| Propylene Glycol | 50.0 | 5.0 | 1.0–10.0 |
| Polyethylene Glycol - 3350, USP | 240.0 | 24.0 | 10.0–40.0 |
| Polyethylene Glycol - 400, USP | 660.0 | 66.0 | 40.0–80.0 |
| qs ad | | | |

Excipient Rationale a. Propylene Glycol, USP—Co-solvent/Preservative; Possible substitutions: Glycerin, ethanol, isopropyl alcohol or other alcohols, polysorbates.

b. Polyethylene Glycol—3350, USP—Viscosity increasing agent; Possible substitutions: Polyethylene glycol—900, 1000, 1450, 4500, 8000 or other high molecular weight glycols, stearyl alcohol, polyoxyl 40 stearate.

c. Polyethylene Glycol—400, USP—Solvent; Possible substitutions: Polyethylene glycol 200, 300, 600, or other low molecular weight glycols.

Method of Manufacture

1. Add a portion (~50%) of the polyethylene glycol-400 to a suitable tared stainless steel mixing bowl fitted with a variable speed agitato and a source of heat.

2. Add the polyethylene glycol-3350 to the bowl and warm gently to ~50° C. with gentle agitation. Continue stirring until the mixture has melted and a complete solution is obtained.

3. Add the propylene glycol, USP and FIAC to the solution in Step 2 and stir to mix well.

4. Q.S. to the final weight with polyethylene glycol-400 and blend to achieve a uniform, clear solution.

5. Remove the heat and permit the solution to cool slowly, continuing gentle agitation until the solution has congealed to a smooth homogeneous ointment and the temperature is below 35° C.

FIAC Solution (1.0–50.0 mg/ml)

| Typical Component | FIAC Ointment, 5% mg/g | % | % Range |
| --- | --- | --- | --- |
| FIAC | 50.0 | 5.0 | 0.1–10.0 |
| Propylene Glycol | 50.0 | 5.0 | 1.0–10.0 |
| Polyethylene Glycol - 3350, USP | 240.0 | 24.0 | 10.0–40.0 |
| Polyethylene Glycol - 400, USP | 660.0 | 66.0 | 40.0–80.0 |
| qs ad | | | |

Excipient Rationale a. Propylene Glycol, USP—Co-solvent/Preservative; Possible substitutions: Glycerin, isopropyl, methanol or other alcohol, polysorbates.

b. Polyethylene Glycol—400, USP—Co-solvent; Possible substitutions: Polyethylene glycol-200, 300, 600, or other low molecular weight glycols.

c. Alcohol, USP—Solvent; Possible substitutions: Alcohol S40-2, isopropyl alcohol or other alcohols.

Method of Manufacture

1. Combine propylene glycol with polyethylene glycol in a suitable container and stir to obtain a uniform solution.

2. Add a portion (~⅔) of the alcohol to step 1 and mix well.

3. Add FIAC to Step 2, rinsing the container well with a portion of the remaining alcohol.

4. Q.S. to the final volume with the alcohol and mix well to obtain a clear solution.

FIAC Petrolatum Ointment (1–50.0 mg/g)

| Typical Component | FIAC Petrolatum Ointment, 1.0% | | |
|---|---|---|---|
| | mg/g | % | % Range |
| FIAC | 10.0 | 1.0 | 0.1–5.0 |
| White Wax | 50.0 | 5.0 | 1.0–10.0 |
| White Petrolatum | 940.0 | 94.0 | 85.0–98.9 |

Excipient Rationale a. White wax—Stiffening agent; Possible substitutions: Yellow wax or beeswax, paraffin wax or other commercial substitutions.

b. White Petrolatum—Ointment Base; Possible substitutions: Yellow Petrolatum or other commercial substitutes.

Method of Manufacture

1. Combine white wax and white petrolatum into a suitable container and heat gently to obtain a clear uniform mixture.

2. Add FIAC to the mixture obtained in Step 1 and mix until thoroughly dispersed (~15 min @80° C.).

3. Remove the heat and permit the solution to cool slowly while mixing until the solution has congealed to a smooth homogeneous ointment and the temperature is below 35° C.

FIAC Cream (1.0–50.9 mg/g)

| Typical Components | FIAC Cream 1.0% | | |
|---|---|---|---|
| | mg/g | % | % Range |
| FIAC | 10.0 | 1.0 | 0.1–5.0 |
| Purified Water, USP | 500.0 | 50.0 | 20.0–80.0 |
| Cetyl Alcohol, USP | 80.0 | 8.0 | 2.0–16.0 |
| Wax, Microcrystalline, USP | 80.0 | 8.0 | 2.0–16.0 |
| Polysorbate 80, USP | 50.0 | 5.0 | 1.0–10.0 |
| Polyethylene Glycol-300, USP | 50.0 | 5.0 | 1.0–10.0 |
| Propylene Glycol, USP | 50.0 | 5.0 | 1.0–10.0 |
| Softisan-601 ® | 60.0 | 6.0 | 1.0–12.0 |
| Stearic Acid, USP | 40.0 | 4.0 | 1.0–10.0 |
| Paraffin, USP | 30.0 | 3.0 | 1.0–6.0 |
| Glyceryl Monostearate, USP | 30.0 | 3.0 | 1.0–6.0 |
| Octoxynol | 20.0 | 2.0 | 0.5–5.0 |

Excipient Rationale a. Purified Water—To aid solubility of the active ingredient and in the formation of the oil in water cream.

b. Cetyl Alcohol—Surface active agent used to stabilize the emulsions and imparts a smooth texture to the skin. Possible substitutions: Stearyl alcohol, octadecanol.

c. Wax Microcrystalline, Softisan ®601, paraffin and stearic acid—Stiffening agents. Possible substitutions: Yellow wax, beeswax or other commercial substitutions.

d. Polysorbate 80—Because of its hydrophilic and lyophilic characteristics it helps as an emulsifying agent. Possible substitutions: fatty acid esters of sorbitol and its anhydrides copolymerized with varying numbers of moles of ethylene oxide.

e. Polyethylene Glycol 300—to aid solubility of the active ingredient. Possible substitutions: other low molecular weight glycols.

f. Propylene Glycol—Solvent/Preservative. Possible substitutions: Glycerin, other alcohols.

g. Glyceryl Monosterate—Emulsifying agent; Possible substitutions: polyolfatty acid esters.

h. Octoxynol—Surfactant and emulsifying agent; Possible substitutions: Nonionic surfactants.

Method of Manufacture a. Clean area and weigh out each component.

b. Add the polysorbate 80, Octoxynol, PEG 300 and propylene glycol together. Add approximately 70% of the FIAC and mix.

c. Melt the paraffin glyceryl monosterate, cetyl alcohol, stearic acid, wax and Softisan ®601 together.

d. Heat the water (50° C.) and add the remainder of the FIAC and stir to dissolve.

e. Heat the oil phase (3) to approximately 80° C.

f. Heat water to 70.

g. Place water under Ross Misier, add the oil phase and mix. As the cream cools, transfer to the kitchen and allow to cool to room temperature with gentle mixing.

FIAC GEL (1.0–50.0 mg/g)

| Typical Components | FIAC Gel, 1.0% | | |
|---|---|---|---|
| | mg/g | % | % Range |
| FIAC | 10.0 | 1.0 | 0.1–5.0 |
| Glycerin, USP | 100.00 | 10.0 | 1.0–25.0 |
| Hydroxypropyl Cellulose, NF | 40.0 | 4.0 | 0.5–8.0 |
| Purified Water, USP | 350.0 | 35.0 | 10.0–70.0 |
| Alcohol, SD40-2 qs ad | 500.0 | 50.0 | 20.0–75.0 |

Excipient Rationale a. Glycerin—Co-solvent/Preservative; Possible substitutions: Propylene glycol, isopropyl alcohol, ethanol, methanol or other alcohols.

b. Hydroxypropyl Cellulose—Gelling Agent; Possible substitutions: Hydroxyethyl cellulose, hydroxypropyl methycellulose, methycellulose or other cellulosic agents, carbomer, polyvinyl alcohol, povidone, gelatin or other commercial substitutions.

c. Purified Water—Co-solvent.

d. Alcohol, SD40-2—Co-solvent; Possible substitutions: Alcohol USP, Isopropyl alcohol, methanol or other alcohols.

Method of Manufacture a. Combine a portion of the water and alcohol (~75% of each) into a suitable container and mix well be Add FIAC to the mixture obtained in step 1 and mix until dissolved.

c. Combine the remaining water and glycerin into a suitable container and heat to approximately 50° C.

d. Add the hydroxypropyl cellulose, slowly, to the water/glycerin mixture (Step 3) to obtain a smooth slurry.

e. Add the hydroxypropyl cellulose slurry to the FIAC solution from Step 2.

f. Q.S. to the final weight with the alcohol and continue mixing for approx. 30 minutes, keeping the container covered to avoid evaporation.

The compositions of the invention are destined for human consumption and implicit in this use is the requirement that the pharmaceutically active substance and any excipients be in a pharmaceutically-acceptable state of purity. Thus, the materials must be free from contaminants or impurities that might cause toxicity or other, adverse problems in humans. The compositions of the invention, particularly those compositions that are meant for parenteral administration, are preferably sterile.

thereby. Such other compositions are considered to be within the scope and spirit of the present invention. Hence, the invention should not be limited by the description of the specific embodiments disclosed herein but only by the following claims.

TABLE II

Adverse Experience Summary

| Body system | Adverse Experience | Severity | Dosage Level (mg/kg-day) 1.0 Incidence | 0.5 Incidence | 0.1 Incidence |
|---|---|---|---|---|---|
| G.I. | Nausea | mild | 6/9 | 3/10 | |
| | Nausea | moderate | 1/9 | 1/10 | |
| | Vomiting | mild | 1/9 | 2/10 | |
| | Diarrhea | mild | 2/9 | 1/10 | |
| | Constipation | mild | 1/9 | | |
| | Heartburn | mild | 1/9 | | |
| | Abdominal Cramping | moderate | 1/9 | | |
| | Light Stools | mild | 1/9 | | |
| Urogenial | Hemauria | moderate | | 1/10 | |
| | Proteinuria | mild | | 1/10 | |
| Musculoskeletal | myositis | severe | 1/9 | | |
| Hepatic | AST elevation | mild (1.25–2.5x) | 4/9 | 3/10 | |
| | AST elevation | moderate (2.5–5.0x) | 1/9 | 1/10 | 2/4 |
| | AST elevation | severe (>5x) | 3/9 | 2/10 | 1/4 |
| | ALT elevation | mild (1.25–2.5x) | 4/9 | 3/10 | |
| | ALT elevation | moderate (2.5–5.0x) | 1/9 | 2/4 | |
| | ALT elevation | severe (>5x) | 3/9 | 2/10 | 1/4 |
| Orofacial | Stomatitis | moderate | | | 1/10 |
| Visual | Difficulty focusing | mild | 1/9 | | |
| Neurologic | Fatigue | mild | 2/9 | 3/10 | |
| | Fatigue | moderate | 1/9 | 1/10 | 1/4 |
| | Fatigue | severe | 1/9 | | |
| | Weakness | mild | 2/9 | 2/10 | |
| | Weakness | moderate | 1/9 | | |
| | Headache | mild | 1/9 | 2/10 | |
| | Headache | moderate | | 1/10 | |
| | Headache | severe | 1/9 | | |
| | Dizziness | mild | 1/9 | | |
| | Disoriented | mild | | 1/10 | |
| | Decreases sensations | mild | 1/9 | | |
| | Paresibesia (extremities) | mild | 1/9 | | |
| Hematologic | Hypophosphatemia | | moderate | 1/10 | |
| | Hyponatremia | mild | | | 1/4 |
| | Hypercalcemia | mild | | | 1/4 |
| | Hypocalcemia | mild | | | 1/4 |
| | Hyperbilirubemia | mild | | | 2/4 |
| | Hypoglycemia | mild | | | 1/4 |

Normally, the formulations will be consumed by the patient in unit or single dosage forms, as for instance in tablets, capsules, caplets, metered doses (obtained for instance using a dosing syringe) from syrups, suspensions or solutions, etc. Such dosage units may be designed to release the drug either for immediate absorption or in a controlled manner to allow the dose to be made available to the body over an extended period of time. Under controlled release conditions, the medium containing the active ingredient may be manipulated to provide an initial burst of active substance followed by a slow steady release or, alternatively, a more or less prolonged constant dose of active substance over time. Such unit or single dosage forms could contain, for instance, 0.05 to 100, preferably 0.05 to 15 or most preferably 0.05 to 5 mg of the active ingredient. Orally acceptable unit or single dosage forms are preferred. An example of such a form would be tablet containing 3 or 5 mg of FIAU. The unit or single dosage forms may contain more than 1 mg of active ingredient. Preferably, the maximum possible daily dosage will not exceed about 25 mg.

It should be apparent to those skilled in the art that other compositions not specifically disclosed in the instant specification are, nevertheless, contemplated

What is claimed:

1. A method of reducing human serum levels of HBV DNA and HBV DNA polymerase which comprises administering to such human a therapeutic amount of a composition comprising a compound of 1-(2'-deoxy-2'-fluoro-β-D-arabinofuroanosyl)-5-iodouracil (FIAU), the prodrug 1-(2'-deoxy-2'-fluoro-β-D-arabinofuranosyl)-5-iodocytosine (FIAC) or the metabolite 1-(2'-deoxy-2'-fluoro-β-D-arabinofuranosyl)uracil (FAU) and a pharmaceutically acceptable carrier.

2. The method of claim 1 in which said composition is administered orally.

3. The method of claim 1 in which said composition is administered parenterally.

4. The method of claim 1 in which said treatment includes one or more administrations of said composition per day for a treatment period of about 7 to about 28 consecutive days.

5. The method of claim 4 in which said treatment period is about 14 consecutive days.

6. The method of claim 1 wherein the therapeutic amount of said composition ranges between about 0.05 to about 1 mg/kg-day.

7. The method of claim 1 wherein said composition contains an amount of said compound selected from the group consisting of about 0.25, 0.5, 1, 2 and 5 mg.

8. A method of reducing serum levels of HBV DNA and HBV DNA polymerase in human patients by administering to said patients a pharmaceutical composition comprising an amount of a compound of 1-(2'-deoxy-2'-fluoro-β-D-arabinofuranosyl)-5-iodouracil (FIAU), the prodrug 1-(2'-deoxy-2'-fluoro-β-D-arabinofuranosyl)-5-iodocytosine (FIAC) or the metabolite 1-(2'-deoxy-2'-fluoro-β-D-arabinofuranosyl)uracil (FAU) and a pharmaceutically acceptable carrier sufficient to provide a dosage of said compound in the range of about 0.05 to 1 mg/kg-day, and a pharmaceutically acceptable carrier.

9. A method for reducing serum levels of HBV DNA and HBV DNA polymerase in human patients by administering to said patients a pharmaceutical composition comprising an amount of the compound FIAU, the prodrug 1-(2'-deoxy-2'-fluoro-β-D-arabinofuranosyl)-5-iodocytosine (FIAC) or the metabolite 1-(2'-deoxy-2'fluoro-β-D-arabinofuranosyl)uracil (FAU) and a pharmaceutically acceptable carrier sufficient to provide said patients with a steady state peak plasma concentration of said compound in the range of about 0.1 to about 1 μg/ml.

10. The method of claim 8 or 9 wherein said composition is administered orally.

11. The method of claim 8 or 9 wherein said composition is administered parenterally.

12. The method of claim 8 or 9 in which said treatment includes one or more administrations of said composition per day for a treatment period of about 7 to about 28 consecutive days.

13. The method of claim 12 in which said treatment period is about 14 consecutive days.

* * * * *